(12) United States Patent
Armitage et al.

(10) Patent No.: US 7,628,851 B2
(45) Date of Patent: Dec. 8, 2009

(54) BONE CEMENT COMPOSITIONS HAVING FIBER-REINFORCEMENT AND/OR INCREASED FLOWABILITY

(75) Inventors: Bryan Monro Armitage, Minneapolis, MN (US); Ira C Ison, San Jose, CA (US); Mark Thomas Fulmer, Glenmoore, PA (US); Sean Hamilton Kerr, Oreland, PA (US); Michael Lehmicke, Media, PA (US); Patrick Leamy, Downingtown, PA (US); William Schiffer, Oxford, PA (US)

(73) Assignee: Synthes USA, LLC, West Chester, PA (US)

( * ) Notice: Subject to any disclaimer, the term of this patent is extended or adjusted under 35 U.S.C. 154(b) by 0 days.

(21) Appl. No.: 12/130,287

(22) Filed: May 30, 2008

(65) Prior Publication Data

US 2008/0226691 A1  Sep. 18, 2008

Related U.S. Application Data

(63) Continuation of application No. 10/936,188, filed on Sep. 7, 2004.

(60) Provisional application No. 60/500,346, filed on Sep. 5, 2003, provisional application No. 60/574,532, filed on May 25, 2004.

(51) Int. Cl.
*A61F 2/28* (2006.01)

(52) U.S. Cl. ............... 106/691; 106/35; 106/776; 106/778; 106/772; 106/774; 106/775; 106/780; 623/23.56; 623/23.51; 623/23.61; 623/23.58; 424/602; 424/603; 424/696

(58) Field of Classification Search ............ 424/602, 424/603, 696; 623/23.61, 23.56, 23.51, 23.58; 106/690, 691, 772, 774–776, 778, 780, 35
See application file for complete search history.

(56) References Cited

U.S. PATENT DOCUMENTS

| | | | |
|---|---|---|---|
| 4,157,437 A | 6/1979 | Okuzumi et al. | |
| 4,172,128 A | 10/1979 | Thiele et al. | |
| 4,503,157 A | 3/1985 | Hatahira | |
| 4,880,610 A | 11/1989 | Constantz | |
| 4,990,333 A | 2/1991 | Lane et al. | |
| 5,047,031 A * | 9/1991 | Constantz | 606/77 |
| 5,053,212 A | 10/1991 | Constantz et al. | |
| 5,129,905 A | 7/1992 | Constantz | |
| 5,152,836 A | 10/1992 | Hirano et al. | |
| 5,164,187 A | 11/1992 | Constantz et al. | |
| 5,178,845 A | 1/1993 | Constantz et al. | |
| 5,279,831 A | 1/1994 | Constantz et al. | |
| 5,336,264 A | 8/1994 | Constantz et al. | |
| 5,496,399 A | 3/1996 | Ison et al. | |
| 5,569,442 A | 10/1996 | Fulmer et al. | |
| 5,571,493 A | 11/1996 | Fulmer et al. | |
| 5,580,623 A | 12/1996 | Fulmer et al. | |
| 5,683,496 A | 11/1997 | Ison et al. | |
| 5,683,667 A | 11/1997 | Fulmer et al. | |
| 5,697,981 A | 12/1997 | Ison et al. | |
| 5,709,742 A | 1/1998 | Fulmer et al. | |
| 5,782,971 A | 7/1998 | Constantz et al. | |
| 5,820,632 A | 10/1998 | Constantz et al. | |
| 5,846,312 A | 12/1998 | Ison et al. | |
| 5,885,540 A | 3/1999 | Fulmer et al. | |
| 5,900,254 A | 5/1999 | Constantz | |
| 5,952,010 A | 9/1999 | Constantz | |
| 5,962,028 A | 10/1999 | Constantz | |
| 5,964,932 A | 10/1999 | Ison et al. | |
| 5,968,253 A * | 10/1999 | Poser et al. | 106/691 |
| 6,002,065 A | 12/1999 | Constantz et al. | |
| 6,005,162 A | 12/1999 | Constantz | |
| 6,027,742 A * | 2/2000 | Lee et al. | 424/422 |
| 6,053,970 A | 4/2000 | Ison et al. | |
| 6,083,229 A | 7/2000 | Constantz et al. | |
| 6,096,855 A | 8/2000 | Sodergard et al. | |
| 6,149,655 A | 11/2000 | Constantz et al. | |
| 6,334,891 B1 | 1/2002 | Constantz et al. | |
| 6,383,190 B1 | 5/2002 | Preissman | |
| 6,955,716 B2 * | 10/2005 | Xu et al. | 106/35 |
| 7,494,950 B2 | 2/2009 | Armitage et al. | |
| 2003/0167093 A1 | 9/2003 | Xu et al. | |
| 2005/0208094 A1 | 9/2005 | Armitage et al. | |

FOREIGN PATENT DOCUMENTS

| | | |
|---|---|---|
| CN | 1285085 | 2/2001 |
| EP | 0714666 A1 | 6/1996 |
| JP | 53-127529 | * 11/1978 |
| JP | 03-085179 | 4/1991 |
| JP | 04-221538 | 8/1992 |
| JP | 07-313586 | 12/1995 |

(Continued)

OTHER PUBLICATIONS

"European Application Serial No. 04809690.3, Office Action mailed May 26, 2008", 6 pgs.
"U.S. Appl. No. 10/936,188, Amendment and Response filed Oct. 26, 2007", 9 pgs.
"U.S. Appl. No. 10/936,188, Non-Final Office Action mailed Oct. 16, 2006", 5 pgs.

(Continued)

*Primary Examiner*—C. Melissa Koslow
(74) *Attorney, Agent, or Firm*—Schwegman, Lundberg & Woessner, P.A.

(57) ABSTRACT

The present invention relates in general to implantable compositions, and method for preparing same, containing a calcium salt-containing component, optionally demineralized bone, a plurality of discrete fibers, optionally a flow additive, and optionally continuous reinforcing fibers or an array of organized fibers in the form of mesh. Advantageously, the discrete fibers have a specific aspect ratio (length/diameter) from about 50:1 to about 1000:1. The addition of a small amount of discrete fibers and/or the continuous reinforcing fibers or fiber mesh can cause drastic increases in certain mechanical properties including flexural strength, flexural toughness, and/or screw pullout strength.

22 Claims, No Drawings

FOREIGN PATENT DOCUMENTS

| | | |
|---|---|---|
| JP | 08-024347 | 1/1996 |
| JP | 09-201330 | 8/1997 |
| JP | 2000262608 A2 | 9/2000 |
| WO | WO-97/36553 | 10/1997 |
| WO | WO-01/32100 A2 | 5/2001 |
| WO | WO-2005/027988 A2 | 3/2005 |

OTHER PUBLICATIONS

"U.S. Appl. No. 10/936,188, Notice of Allowance mailed Apr. 19, 2007", 3 pgs.

"U.S. Appl. No. 10/936,188, Notice of Allowance mailed Sep. 14, 2007", 3 pgs.

"U.S. Appl. No. 10/936,188, Response Filed Jan. 16, 2007 to Non-Final Office Action mailed Oct. 16, 2006", 11 pgs.

"U.S. Appl. No. 10/936,188 Notice of Allowance mailed Mar. 24, 2008", 4 pgs.

"Chinese Patent Application No. 200480032523.9, First Office Action mailed Nov. 23, 2007", 4 pgs.

"Chinese Patent Application No. 200480032523.9, Response filed Apr. 8, 2008 to First Office Action mailed Nov. 23, 2007", 16 pgs.

"European Patent Application No. 04809690.3, Examination Report mailed Jul. 21, 2006", 5 pgs.

"European Patent Application No. 04809690.3, Response filed Jan. 25, 2007 to Examination Report mailed Jul. 21, 2006", 63 pgs.

"PCT Application No. PCT/US2004/029098, International Search Report mailed May 6, 2005", 3 pgs.

"PCT Application No. PCT/US2004/029098, Written Opinion mailed May 6, 2005", 5 pgs.

"PCT Application No. PCT/US2004/0299098, International Preliminary Report on Patentability mailed Mar. 6, 2006".

Xu, H. H., et al., "Calcium Phosphate Cement Containing Resorbable Fibers for Short-Term Reinforcement and Macroporosity", *Biomaterials*, 23(1), (Jan. 2002), 193-202.

Xu, H. H., et al., "Reinforcement of a Self-Setting Calcium Phosphate Cement With Different Fibres", *Journal of Biomedical Materials Research—Part A*, vol. 52(1), (Oct. 2002), 107-114.

"European Patent Application No. 04750971.6, Communication mailed Jun. 12, 2008", 5 pgs.

"Japanese Application No. 2002-506661, Notice of the Reason for the Rejection mailed Feb. 27, 2008", (w/ English Translation), 7 pgs.

"Japanese Application No. 2002-506661, Official Notice of Reason for the Final Rejection mailed Jul. 11, 2008", (w/ English Translation), 4 pgs.

Kaneko, Y., et al., "Synthesis and Swelling—deswelling kinetics of poly(N-isopropylacrylamide) hydrogels grafted with LCST modulated polymers", *Journal of Biomaterials Science, Polymer Edition*, 10(11), (1999), 1079-1091.

Stile, R. A., et al., "Synthesis and Characterization of Injectable Poly(N-isopropylacrylamide)-Based Hydrogels That Support Tissue Formation in Vitro", *Macromolecules*, 32, (1999), 7370-7379.

Zhu, Y. T., et al., "Bone-Shaped Short Fiber Composites—An Overview", *Materials Science and Engineering: A*, 326(2), (2002), 208-227.

"Australia Application No. 2004273794, Examiner report Mailed on Apr. 16, 2009", 3 pgs.

* cited by examiner

BONE CEMENT COMPOSITIONS HAVING FIBER-REINFORCEMENT AND/OR INCREASED FLOWABILITY

RELATED APPLICATIONS

This application is a Continuation of U.S. patent application Ser. No. 10/936,188 filed on Sep. 7, 2004, and titled "BONE CEMENT COMPOSITIONS HAVING FIBER-REINFORCEMENT AND/OR INCREASED FLOWABILITY" which claims the benefit of U.S. Provisional Application No. 60/500,346, filed Sep. 5, 2003 and U.S. Provisional Application No. 60/574,532, filed May 25, 2004, the entire disclosure of each of the aforementioned applications being incorporated by reference herein in their entirety.

FIELD OF THE INVENTION

The present invention relates in general to implantable compositions, and methods for preparing same, containing a calcium salt-containing component, a plurality of discrete fibers, optionally demineralized bone, optionally a flow additive, and optionally continuous reinforcing fibers or an array of organized fibers in the form of a mesh. Advantageously, the discrete fibers have a specific aspect ratio (length/diameter) from about 50:1 to about 1000:1. The addition of a small amount of discrete fibers and/or the continuous reinforcing fibers or fiber mesh can cause drastic increases in certain mechanical properties including flexural strength, flexural toughness, and/or screw pullout strength.

BACKGROUND OF THE INVENTION

One particular area of interest with regard to bone cements or calcium phosphate compositions focuses on the addition of viscosity-modifying agents to make the compositions liquid-like or flowable. Flowability is a consideration especially when the bone cements or calcium phosphate compositions are used as an aid to filling voids in bone, to treating bone defects, or to augment the stability of other implantable devices in vivo. Without adequate flowability, bone cements typically are molded by hand to fit a particular bone void or defect. However, non-flowable cements cannot be used when it is necessary or desired to fill a hole, void, or defect in a bone larger than the area from which a surgeon can access the hole, void, or defect. In addition, non-flowable cements cannot be easily created in situ to fill a particular hole, void, or defect, but must be prefabricated. If the molded bone cement does not fit or cannot be forced to do so by external pressure of a surgeon once relatively in place, it does not create a sufficient implantable construct to facilitate healing and/or bone regrowth.

Another particular area of interest with regard to bone cements or calcium phosphate compositions focuses on reinforcing its bone cements with fibers, usually relatively long fibers, or fiber meshes. Much of the prior art in implantable composite materials focuses on a strong and resilient matrix impregnated with reinforcing filler particles, whiskers, or meshes. Often the ceramic bone cements are strong enough but are brittle and not sufficiently resistant to catastrophic failure (e.g., through cracking) to function as the matrix material. Polymers, usually resorbable, generally perform that reinforcing function. Resorbable implant materials, such as polylactides and polyglycolides, as compared to traditional, non-resorbable metal or composite materials, for example, have the advantage of being biocompatible, of being biodegradable after a period of time, and of not requiring removal, e.g., in bone fixation or repair applications. These qualities are especially important for implant matrices that are designed to be temporary place fillers (and in some cases, stabilizing components) for healing and/or regrowth, e.g., of bone voids or defects.

In addition, with most composites, the reinforcing material is different than the matrix material, in the hopes that the most beneficial set of properties can be amplified from each component, while the less desirable characteristics of each component are preferably reduced. As a result, the fibers used are generally ceramic in nature or of a (co)polymer composition of different chemistry. However, there is little prior art addressing implantable materials containing resorbable or biodegradable fibers in a ceramic matrix. One example of fiber-reinforced ceramic matrices can be found in a Xu et al. article entitled "Reinforcement of a Self-Setting Calcium Phosphate Cement with Different Fibers," in *J. Biomed. Mater. Res.*, 2000, vol. 52, pp. 107-114 ("the Xu article").

The Xu Article discloses water-based calcium phosphate cements that were reinforced with fibers of aramid (KEVLAR), carbon, E-glass, and POLYGLACTIN. It discloses fiber lengths of 3 mm, 8 mm, 25 mm, 75 mm, and 200 mm, with fiber volume fraction loadings of 1.9%-9.5% in CPC powder, which contains a mixture of tetracalcium phosphate and anhydrous dicalcium phosphate, which react in an aqueous environment to form hydroxyapatite. The POLYGLACTIN fibers in the Xu article are 90/10 copolymers of glycolide/lactide and had a measured diameter of about 200 microns.

It is, therefore, desirable to obtain a fiber-reinforced and/or flowable calcium salt-containing composite material for implantation that exhibits improvements in key mechanical properties as a result of a specific combination of properties of the ingredients, particularly fiber length, fiber diameter or width, fiber aspect ratio, flow additive incorporation, continuous fiber/stent/mesh incorporation, or the like, or a combination of multiple variables.

SUMMARY OF THE INVENTION

One aspect of the invention relates to an implantable composition comprising: (a) a calcium salt-containing component, preferably a calcium phosphate containing component, including amorphous calcium phosphate, crystalline calcium phosphate, $CaHPO_4$, $CaHPO_4.H_2O$, $\alpha\text{-}Ca_3(PO_4)_2$, $\alpha\text{-bar-}Ca_3(PO_4)_2$, $\beta\text{-}Ca_3(PO_4)_2$, $\gamma\text{-}Ca_3(PO_4)_2$, $Ca_5(PO_4)_3OH$, $Ca_{10}(PO_4)_6(OH)_2$, $Ca_4O(PO_4)_2$, $CaP_4O_{11}$, $\alpha\text{-}Ca_2P_2O_7$, $\beta\text{-}Ca_2P_2O_7$, $\gamma\text{-}Ca_2P_2O_7$, $Ca(H_2PO_4)_2.nH_2O$, where n is a real number from 0 to 5, $Ca_8H_2(PO_4)_6.5H_2O$ or calcium pyrophosphate; calcium sulfates including $Ca(SO_4)_2$, $\alpha\text{-}Ca(SO_4)_2.1/2H_2O$, $\beta\text{-}Ca(SO_4)_2 .1/2H_2O$; or any combination thereof; and (b) discrete fibers that are resorbable homopolymers or copolymers (particularly from about 1% to about 5% by weight) that have an aspect ratio from about 50:1 to about 1000:1 and that have a fiber length of about 15 mm or less. In one embodiment, the implantable composition further comprises demineralized bone. In another embodiment, the composition may include continuous reinforcing fibers. Advantageously, the composition according to the invention can further comprise a flow additive including, but not limited to, hyaluronic acid, a hyaluronate salt, a sodium phosphate salt, or a combination thereof (optionally also including continuous reinforcing fibers).

In another embodiment, the calcium salt-containing component can consist essentially of a bone cement comprising monocalcium phosphate monohydrate, α-tricalcium phosphate, and calcium carbonate as solid components, and from about 0.01 to about 0.2 mol/kg of a sodium phosphate salt in solution as a liquid component. In one preferred case of this embodiment, the monocalcium phosphate monohydrate can be present in an amount of about 3.3% by weight of the solid components, the α-tricalcium phosphate in an amount of about 84.4% by weight of the solid components, and the calcium carbonate in an amount of about 12.3% by weight of the solid components. In another embodiment, the sodium phosphate salt can be present in an amount of about 0.15 mol/kg of solution, and the ratio of liquid component(s) to solid components can be from about 0.48 to about 0.65, from about 0.52 to about 0.60, or about 0.56. In another embodiment, the sodium phosphate salt can be present in an amount of about 0.075 mol/kg of solution, and the ratio of liquid component(s) to solid components can be from about 0.41 to about 0.55, from about 0.47 to about 0.53, or about 0.50.

In another embodiment, the calcium salt-containing component can consist essentially of a bone cement comprising monocalcium phosphate monohydrate, α-tricalcium phosphate, calcium carbonate, barium sulfate, and from about 0.01 to about 0.2 mol/kg of a sodium phosphate salt. In one preferred case of this embodiment, the monocalcium phosphate monohydrate can be present in an amount of about 2.9% by weight of the solid components, the α-tricalcium phosphate in an amount of about 73.4% by weight of the solid components, the calcium carbonate in an amount of about 10.7% by weight of the solid components, and the barium sulfate in an amount of about 13% by weight of the solid components. In another case of this embodiment, the sodium phosphate salt can be present in an amount of about 0.075 mol/kg of solution, and the ratio of liquid component(s) to solid components can be from about 0.41 to about 0.55, preferably about 0.50, or from about 0.42 to about 0.47, preferably about 0.45.

In another embodiment, the composition as a whole exhibits increases over the calcium salt-containing component and the flow additive components alone in flexural strength from about 50% to about 900%, in screw pullout strength from about 75% to about 800%, in flexural toughness of at least about 35-fold, or in some combination thereof. Additionally or alternately, the composition as a whole exhibits increases in flexural strength over the calcium salt-containing component and the flow additive components alone from about 200% to about 700%. Additionally or alternately, the composition as a whole exhibits increases in screw pullout strength over the calcium salt-containing component and the flow additive components alone from about 150% to about 600%. Additionally or alternately, the composition as a whole exhibits increases in flexural toughness over the calcium salt-containing component and the flow additive components alone of at least 50-fold.

In another embodiment, the invention relates to an implantable composition comprising solid and liquid components in the form of the following: (a) a calcium salt-containing component comprising: amorphous calcium phosphate, crystalline calcium phosphate, $CaHPO_4$, $CaHPO_4.H_2O$, $\alpha\text{-}Ca_3(PO_4)_2$, $\alpha\text{-bar-}Ca_3(PO_4)_2$, $\beta\text{-}Ca_3(PO_4)_2$, $\gamma\text{-}Ca_3(PO_4)_2$, $Ca_5(PO_4)_3OH$, $Ca_{10}(PO_4)_6(OH)_2$, $Ca_4O(PO_4)_2$, $CaP_4O_{11}$, $\alpha\text{-}Ca_2P_2O_7$, $\beta\text{-}Ca_2P_2O_7$, $\gamma\text{-}Ca_2P_2O_7$, $Ca(H_2PO_4)_2.nH_2O$, where n is a real number from 0 to 5, $Ca_8H_2(PO_4)_6.5H_2O$ or calcium pyrophosphate; calcium sulfates including $Ca(SO_4)_2$, $\alpha\text{-}Ca(SO_4)_2.1/2H_2O$, $\beta\text{-}Ca(SO_4)_2.1/2H_2O$; or any combination thereof; and (b) a plurality of discrete resorbable homopolymer or copolymer fibers having a fiber length of not more than about 15 mm. In one embodiment, the implantable composition further comprises demineralized bone. Advantageously, the ratio of liquid components to solid components in the implantable composition can be from about 0.41 to about 0.55, and the implantable composition can exhibit increases over the calcium salt-containing component and the optional flow additive in flexural strength from about 50% to about 900%, in screw pullout strength from about 75% to about 800%, in flexural toughness of at least about 35-fold, or in some combination thereof.

In another embodiment, the invention relates to an implantable composition comprising solid and liquid components in the form of the following: (a) a calcium salt-containing component comprising: amorphous calcium phosphate, crystalline calcium phosphate, $CaHPO_4$, $CaHPO_4.H_2O$, $\alpha\text{-}Ca_3(PO_4)_2$, $\alpha\text{-bar-}Ca_3(PO_4)_2$, $\beta\text{-}Ca_3(PO_4)_2$, $\gamma\text{-}Ca_3(PO_4)_2$, $Ca_5(PO_4)_3OH$, $Ca_{10}(PO_4)_6(OH)_2$, $Ca_4O(PO_4)_2$, $CaP_4O_{11}$, $\alpha\text{-}Ca_2P_2O_7$, $\beta\text{-}Ca_2P_2O_7$, $\gamma\text{-}Ca_2P_2O_7$, $Ca(H_2PO_4)_2.nH_2O$, where n is a real number from 0 to 5, $Ca_8H_2(PO_4)_6.5H_2O$ or calcium pyrophosphate; calcium sulfates including $Ca(SO_4)_2$, $\alpha\text{-}Ca(SO_4)_2.1/2H_2O$, $\beta\text{-}Ca(SO_4)_2.1/2H_2O$; or any combination thereof; (b) a plurality of discrete resorbable homopolymer or copolymer fibers; and (c) continuous reinforcing fibers comprising an array or mesh of resorbable homopolymer or copolymer fibers. In another embodiment, the implantable composition further comprises demineralized bone. Advantageously, the ratio of liquid components to solid components in the implantable composition can be from about 0.41 to about 0.55, and the implantable composition can exhibit increases over the implantable composition without the plurality of discrete fibers in flexural strength from about 50% to about 900%, in screw pullout strength from about 75% to about 800%, in flexural toughness of at least about 35-fold, or in some combination thereof.

Another aspect of the invention relates to an implantable composition comprising: (a) a calcium salt-containing component comprising: amorphous calcium phosphate, crystalline calcium phosphate, $CaHPO_4$, $CaHPO_4.H_2O$, $\alpha\text{-}Ca_3(PO_4)_2$, $\alpha\text{-bar-}Ca_3(PO_4)_2$, $\beta\text{-}Ca_3(PO_4)_2$, $\gamma\text{-}Ca_3(PO_4)_2$, $Ca_5(PO_4)_3OH$, $Ca_{10}(PO_4)_6(OH)_2$, $Ca_4O(PO_4)_2$, $CaP_4O_{11}$, $\alpha\text{-}Ca_2P_2O_7$, $\beta\text{-}Ca_2P_2O_7$, $\gamma\text{-}Ca_2P_2O_7$, $Ca(H_2PO_4)_2.n\ H_2O$, where n is a real number from 0 to 5, $Ca_8H_2(PO_4)_6.5H_2O$ or calcium pyrophosphate; calcium sulfates including $Ca(SO_4)_2$, $\alpha\text{-}Ca(SO_4)_2.1/2H_2O$, $\beta\text{-}Ca(SO_4)_2.1/2H_2O$; or any combination thereof; and (b) a plurality of discrete, resorbable, homopolymer or copolymer fibers that have an aspect ratio from about 50:1 to about 500:1, wherein the ends of the fibers have been modified to form beads, balls, dogbone shapes, or dumbbell shapes, the fibers have been textured to increase pullout resistance (e.g., kinking or crimping the fiber), or combinations thereof. In another embodiment, the implantable composition further comprises demineralized bone. Advantageously, the composition also includes continuous reinforcing fibers. In another embodiment, the composition according to the invention can further comprise a flow additive including hyaluronic acid, a hyaluronate salt, a sodium phosphate salt, or a combination thereof; and optionally continuous reinforcing fibers.

In another embodiment, the invention relates to an implantable composition comprising solid and liquid components in the form of the following: a calcium salt-containing component consisting essentially of a bone cement comprising monocalcium phosphate monohydrate, α-tricalcium phosphate, calcium carbonate; demineralized bone, and from about 0.01 to about 0.2 mol/kg of a sodium phosphate salt; and a sufficient amount of a flow additive comprising hyaluronic acid, a hyaluronate salt, a sodium phosphate salt, or a combination thereof to allow the implantable composition to flow through a syringe needle having a gauge from about 12 to about 18 with a maximum injection pressure of not more than about 40 pounds, wherein the ratio of liquid components to solid components in the implantable composition is from about 0.41 to about 0.55. In one embodiment, the composition also includes continuous reinforcing fibers. Advantageously, the composition according to the invention can further comprise a plurality of discrete resorbable homopolymer or copolymer fibers having a fiber length of not more than about 15 mm, an aspect ratio from about 50:1 to about 1000:1, or both (and optionally also include continuous reinforcing fibers).

Another aspect of the invention relates to a process for making an implantable composition that is at least partially biodegradable, at least partially resorbable, at least partially biocompatible, or a combination thereof, which process comprises the following steps: (a) incorporating a flow additive with a calcium salt-containing component to form a flowable calcium salt-containing composition that can be injected through a syringe needle having a gauge size of about 12 or greater with a maximum injection pressure of not more than about 40 pounds; and (b) incorporating a plurality of discrete fibers with the flowable calcium phosphate-containing composition to form a fiber-reinforced, calcium salt-containing component. In one embodiment, the flowable calcium salt-containing composition can further comprise demineralized bone. Advantageously, the plurality of discrete fibers can be resorbable homopolymers or copolymers having an aspect ratio from about 50:1 to about 1000:1 and a fiber length of not more than about 15 mm.

Another aspect of the invention relates to a process for providing an implantable composition that is at least partially biodegradable, at least partially resorbable, at least partially biocompatible, or a combination thereof, which process comprises the following steps: (a) incorporating a plurality of discrete fibers, with a calcium salt-containing component or a flowable calcium salt-containing composition to form a fiber-reinforced, calcium salt-containing component; and (b) introducing the fiber-reinforced, calcium salt-containing component into, onto, and/or proximal to the bone void and/or the bone defect in order to at least partially coat and/or fill the bone void and/or the bone defect, thus forming an implantable fiber-reinforced composite material. In one embodiment, demineralized bone is incorporated into the fiber-reinforced, calcium salt-containing component. Advantageously, the plurality of discrete fibers can be resorbable homopolymers or copolymers having both an aspect ratio from about 50:1 to about 1000:1 and a fiber length of not more than about 15 mm.

Also advantageously, the implantable fiber-reinforced composite material can exhibit increases over the flowable calcium phosphate-containing composition in flexural strength from about 50% to about 900%, in screw pullout strength from about 75% to about 800%, in flexural toughness of at least about 35-fold, or in some combination thereof; or both.

In one embodiment, the process further comprises grinding the calcium salt-containing component. Additionally or alternately, the process further comprises incorporating a flow additive with the calcium salt-containing component to form the flowable calcium phosphate-containing composition that can be injected through a syringe needle having a gauge size of about 12 or greater with an injection pressure of not more than about 40 pounds. Additionally or alternately, the process further comprises treating a bone void, a bone defect, an in vivo area proximal thereto, or some combination thereof, for receiving the implantable composition. Additionally or alternately, the process further comprises positioning and/or anchoring continuous reinforcing fibers near, around, and/or within a bone void, a bone defect, an in vivo area proximal thereto, or some combination thereof. Additionally or alternately, the process further comprises treating the at least partially coated and/or filled bone void and/or bone defect containing the implantable fiber-reinforced composite material and/or the in vivo area proximal thereto to form a biocompatible and/or semi-permeable surface.

Another aspect of the invention relates to a process for providing an implantable composition that is at least partially biodegradable, at least partially resorbable, at least partially biocompatible, or a combination thereof, which process comprises the following steps: (a) incorporating a flow additive with a calcium salt-containing component to form a flowable calcium salt-containing composition that can be injected through a syringe needle having a gauge size of about 12 or greater with a maximum injection pressure of not more than about 40 pounds; (b) incorporating a plurality of discrete fibers with the flowable calcium phosphate-containing composition to form a fiber-reinforced, calcium salt-containing component; and (c) introducing the flowable calcium phosphate-containing composition or a fiber-reinforced, calcium salt-containing component into, onto, and/or proximal to the bone void and/or the bone defect in order to at least partially coat and/or fill the bone void and/or the bone defect, thus forming an implantable composite material. In one embodiment, the flowable calcium salt-containing composition can further comprise demineralized bone. Advantageously, the plurality of discrete fibers can be resorbable homopolymers or copolymers having an aspect ratio from about 50:1 to about 1000:1 and a fiber length of not more than about 15 mm. Also advantageously, the implantable composite material can exhibit increases over the flowable calcium phosphate-containing composition in flexural strength from about 50% to about 900%, in screw pullout strength from about 75% to about 800%, in flexural toughness of at least about 35-fold, or in some combination thereof; or both.

In one embodiment, the process further comprises grinding the calcium salt-containing component. Additionally or alternately, the process further comprises treating a bone void, a bone defect, an in vivo area proximal thereto, or some combination thereof, for receiving the implantable composition. Additionally or alternately, the process further comprises positioning and/or anchoring continuous reinforcing fibers near, around, and/or within a bone void, a bone defect, an in vivo area proximal thereto, or some combination thereof. Additionally or alternately, the process further comprises treating the at least partially coated and/or filled bone void and/or bone defect containing the implantable fiber-reinforced composite material and/or the in vivo area proximal thereto to form a biocompatible and/or semi-permeable surface. In one embodiment, the implantable composition can further comprise demineralized bone.

DETAILED DESCRIPTION OF THE PREFERRED EMBODIMENTS

One aspect of the present invention relates to a composition comprising a calcium salt-containing component (e.g., a bone cement), and a plurality of discrete fibers and optionally continuous reinforcing fibers or fiber mesh for use as a fiber-reinforced bone cement in any of a number of applications. In another aspect of the invention, the composition further comprises demineralized bone.

The compositions according to the present invention are typically meant to be used in bioabsorbable and/or resorbable applications, implantable medical devices, and the like. Specifically, such applications or devices can include, but are not limited to, (bone) void filler, adjunct to bone fracture stabilization, intramedullary fixation device, pin, anchor, "injectable nail" (e.g., for use in metaphyseal and/or diaphyseal regions of bone), "injectable screw," and the like, in place of and/or in combination with one or more other conventional devices, which can include, but are not limited to, bone fixation plates (e.g., craniofacial, maxillofacial, orthopedic, skeletal, or the like), screws, tacks, clips, staples, nails, pins or rods, anchors (e.g., for suture, bone, or the like), scaffolds, stents, meshes (e.g., rigid, expandable, woven, knitted, weaved, etc.), sponges, implants for cell encapsulation or tissue engineering, or delivery of a drug or a therapeutic substance as discussed below (e.g., carriers, bone ingrowth induction catalysts such as bone morphogenetic proteins, growth factors, peptides, and the like, antivirals, antibiotics, etc.), monofilament or multifilament structures, sheets, coatings, membranes (e.g., porous, microporous, resorbable, etc.), foams (e.g., open cell or closed cell), screw augmentation, cranial reconstruction, and/or combinations thereof.

The implantable composition can be molded (e.g., a paste or putty) or injected. The implantable composition of the present invention hardens into a solid which may be machined using standard orthopedic tools. For example, the hardened composition can be drilled to accept screws or pins, or can be shaped using standard orthopedic abrasive or cutting tools. The composition may be manipulated such as by machining and drilling without fragmenting.

The calcium salt-containing component is typically a bone cement, but can advantageously contain one or more of the following calcium phosphate compounds: $CaHPO_4$ (this compound is generally referred to as monetite or anhydrous dicalcium phosphate), $CaHPO_4.H_2O$, $Ca_3(PO_4)_2$ (e.g., α-, α-bar-, β-, or γ-crystalline forms), $Ca_5(PO_4)_3OH$, $Ca_{10}(PO_4)_6(OH)_2$, $Ca_4O(PO_4)_2$, $CaP_4O_{11}$, $Ca_2P_2O_7$, $Ca_8H_2(PO_4)_6.5H_2O$, $Ca(H_2PO_4)_2.nH_2O$ (e.g., where n=1, this compound is generally referred to as monocalcium phosphate monohydrate; where n=0, this compound is generally referred to as monocalcium phosphate anhydrous), calcium pyrophosphate, or the like. In some embodiments, in the calcium salt-containing component, the Ca can be partially substituted by at least one other element including, but not limited to, Sr, Ba, Mg, Fe, Al, Y, Li, Na, K, Ag, Pd, Zn, Pb, Cd, H, Co, Ni, Mn, or another rare earth metal. In some other embodiments, the ($PO_4$) moiety can additionally or alternately be totally or partially substituted by at least one other moiety including, but not limited to, $PO_3$, $VO_4$, $BO_3$, $SO_4$, $CO_3$, $SiO_4$, or the like, or a combination thereof. In still other embodiments, the (OH) moiety, if present, can additionally or alternately be partially substituted by at least one other moiety including, but not limited to, F, Cl, O, $CO_3$, I, Br, or the like, or a combination thereof. The calcium salt-containing component can include or be in the form of a homogeneous solid solution, a substitutional solid solution, an interstitial solid solution, a general crystalline product, an amorphous product, or the like, or a combination thereof, and can additionally or alternately include a non-stoichiometric defect.

In an alternate embodiment, the calcium salt-containing component can comprise non-calcium phosphate-containing components, which include, but are not limited to, a calcium phosphite; a calcium carbonate; a calcium sulfate such as $Ca(SO_4)_2$, α-$Ca(SO_4)_2$.$1/2H_2O$ or β-$Ca(SO_4)_2$ .$1/2H_2O$; a calcium silicate; calcite; hydrocalcite; aragonite; or the like, or a combination thereof.

In one preferred embodiment, the calcium salt-containing component is a β-tricalcium phosphate-based bone cement composition. In an alternate preferred embodiment, the calcium salt-containing component is an α-tricalcium phosphate-based bone cement composition. In another alternate preferred embodiment, the calcium salt-containing component is a hydroxyapatite-based bone cement composition. In still another alternate preferred embodiment, the calcium salt-containing component is a crystalline $CaHPO_4$-based bone cement composition. In an alternate embodiment, the calcium salt-containing component is an amorphous calcium phosphate-based bone cement composition. In another embodiment, the calcium salt-containing component does not contain tetracalcium phosphate. In yet another embodiment, the calcium salt-containing component does not contain anhydrous dicalcium phosphate. In still another embodiment, the calcium salt-containing component does not contain the combination of tetracalcium phosphate and anhydrous dicalcium phosphate.

In a more preferred embodiment, the calcium salt-containing component is a bone cement composition as described in any of the following U.S. Pat. Nos. 4,503,157; 4,880,610; 5,047,031; 5,053,212; 5,129,905; 5,164,187; 5,178,845; 5,279,831; 5,336,264; 5,496,399; 5,569,442; 5,571,493; 5,580,623; 5,683,496; 5,683,667; 5,697,981; 5,709,742; 5,782,971; 5,820,632; 5,846,312; 5,885,540; 5,900,254; 5,952,010; 5,962,028; 5,964,932; 5,968,253; 6,002,065; 6,005,162; 6,053,970; 6,334,891; or some combination thereof, the entire contents of which are hereby incorporated by express reference hereto.

In another preferred embodiment, the calcium salt-containing component is a bone cement that contains monocalcium phosphate monohydrate, or $Ca(H_2PO_4)_2.H_2O$, α-tricalcium phosphate, or $Ca_3(PO_4)_2$, and/or calcium carbonate, or $CaCO_3$, as well as a setting solution including a sodium phosphate salt and/or buffer (e.g., with the salt and/or buffer component(s) having a concentration from about 0.01 to about 0.2 mol/kg).

Unless otherwise defined herein, the phrase "sodium phosphate" means $Na_3HPO_4$, $Na_2HPO_4$, $NaH_2PO_4$, or any combination thereof.

In one embodiment, the calcium-salt containing component further comprises barium apatite ($Ba_5(OH)(PO_4)_3$).

As noted above, the implantable composition of the invention can comprise a liquid component(s) as described below. The ratio of liquid component(s) to calcium salt-containing component and, when used, demineralized bone, can vary. In one embodiment, the ratio of liquid to calcium salt-containing component and, when used, demineralized bone, is from about 0.4 to about 0.75; in another embodiment from 0.45 to about 0.65, preferably about 0.50; and in another embodiment from 0.55 to about 0.65 by weight based on the weight of the implantable composition.

The pH of the calcium salt-containing component is usually neutral (or only very mildly acidic) or basic. In one embodiment, the pH of the calcium salt-containing component can be from about 6.5 to about 10.5. In another embodiment, the pH of the calcium salt-containing component can be from about 6.8 to about 10, from about 7 to about 9.5, or from about 7.2 to about 9.5.

While acidic components are not always desired in bone cements, the calcium salt-containing component according to the invention can optionally contain a relatively small amount of an inorganic and/or an organic acid, preferably an organic acid. In such cases, any organic acid can be used, with specific examples thereof including, but not limited to, acetic acid, adipic acid, ascorbic acid, benzoic acid, butyric acid, citric acid, cinnamic acid, formic acid, fumaric acid, gallic acid, gluconic acid, glutamic acid, glutaric acid, glyceric acid, glycolic acid, glycolic acid, glyconic acid, hydroxycinnamic acid, isobutyric acid, isophthalic acid, lactic acid, malonic acid, maleic acid, malic acid, naphthoic acid, oxalic acid, phthalic acid, picolinic acid, propionic acid, salicylic acid, sebacic acid, succinic acid, tartaric acid, terephthalic acid, or the like, or combinations thereof. Preferred organic acids can include, but are not limited to, α-hydroxy acids such as glycolic acid, lactic acid, and the like, acetic acid, ascorbic acid, and combinations thereof In one embodiment, the acidic component includes citric acid. In another embodiment, the acidic component does not include citric acid. Examples of inorganic acids that can be used alternately or in addition to organic acids include, but are not limited to, nitric acid, nitrous acid, hydrochloric acid, sulfuric acid, singly ionized sulfuric acids such as $NaHSO_4$, $KHSO_4$, $Ca(HSO_4)_2$, or the like, phosphoric acid, singly or doubly ionized phosphoric acids such as $NaH_2PO_4$, $KH_2PO_4$, $LiH_2PO_4$, $Li_2HPO_4$, $Na_2HPO_4$, $K_2HPO_4$, $MgHPO_4$, or the like, phosphonic acids, ammoniated versions of the above acids (e.g., ammonium nitrate, ammonium chloride, diammonium sulfate, ammonium hydrogen sulfate, triammonium phosphate, diammonium hydrogen phosphate, ammonium dihydrogen phosphate, etc.), or the like, or combinations thereof. When present, the acid component in the bone cement is generally less than about 5% by weight, preferably less than about 4% by weight, e.g., from about 0.2% to about 1.5% by weight, from about 2% to about 4% by weight, from about 2.5% to about 3.5% by weight, or from about 0.1% to about 1% by weight, of the calcium salt-containing component or bone cement.

In one embodiment, the concentration of the calcium salt-containing component in the composition is greater than about 30%, for example greater than about 40%, greater than about 41%, greater than about 45%, or greater than about 50%. In another embodiment, the concentration of the calcium salt-containing component in the composition is less than about 80%, for example less than about 70%, or less than about 60%. In another embodiment, the concentration of the calcium salt-containing component in the composition can be from about 40% to about 60%, alternately from about 47% to about 53%, from about 42% to about 47%, from about 52% to about 57%, or from about 45% to about 50%. In still another embodiment, the concentration of the calcium salt-containing component in the composition can be from about 48% to about 58%, from about 42% to about 50%, or preferably about 50%.

As noted above, the implantable composition can, in certain embodiment, comprise demineralized bone. As used herein, the term "demineralized bone" refers to bone having less than about 8% by weight of its original mineral content.

Demineralized bone is available from Grafton Osteotech, Eatontown, N.J. or Musculoskeletal Transplant Foundation, Edison, N.J.; or can be prepared by treating bone with dilute mineral acid such as, e.g., hydrochloric acid, hydrobromic acid, hydroiodic acid, or sulfuric acid; chelating agents; or complex compound-forming acids such as citric acid, lactic acid, or hypophosphorous acid. See U.S. Pat. Nos. 4,172,128 to Thiele et al.; and 4,990,333 to Lane et al. The demineralized bone can be sourced from any animal. In one embodiment, the demineralized bone is sourced from bovine or human bone. In another embodiment, demineralized bone is sourced from human bone.

In one embodiment, the demineralized bone is sourced from the patient's own bone (autogenous bone).

In another embodiment, the demineralized bone is sourced from a different animal (including a cadaver) of the same species (allograft bone).

In one embodiment, the implantable composition comprises a mixture of demineralized bone and a calcium salt-containing component. When the implantable composition comprises a mixture of demineralized bone and a calcium salt-containing component, the amount of demineralized bone can vary. In one embodiment, the amount of demineralized bone is from about 0.05% to about 30% by weight based on the total amount of demineralized bone and calcium salt-containing component; in another embodiment, the amount of demineralized bone is from about 1% to about 20% by weight based on the total amount of demineralized bone and calcium salt-containing component; and in another embodiment, the amount of demineralized bone is from about 1% to about 10% by weight based on the total amount of demineralized bone and calcium salt-containing component.

Any suitable particle size of demineralized bone can be used. For example, the particle size of the demineralized bone typically is from about 50 to about 850 microns. In another embodiment, the particle size of the demineralized bone is from about 210 to about 600 microns Demineralized bone of a desired particle size can be obtained by known methods such as, e.g., milling and sieving (see *Perry's Chemical Engineering Handbook,* chapter 21, pages 12-19 (Don W. Green, ed. 1984)).

In another embodiment, the implantable composition can further comprise a radiopaque agent to provide a radiopaque cement. Non-limiting examples of radiopaque agents include barium sulfate, barium apatite, and iodine. In one embodiment, the implantable composition comprises barium sulfate.

The fibers according to the invention can be either resorbable or nonresorbable (but nevertheless are typically at least biocompatible) in vivo.

In another embodiment, the aspect ratio of the fibers can be from about 50:1 to about 950:1, from about 50:1 to about 750:1, from about 50:1 to about 500:1, from about 50:1 to about 250:1; or from about 50:1 to about 100:1.

In another embodiment, the length of the fibers can be not more than about 8.5 mm. In another embodiment, the length of the fibers can be at least about 2.5 mm. In another embodiment, the length of the fibers can be from about 2.5 mm to about 8.5 mm. In another embodiment, the length of the fibers can be from about 0.5 mm to about 1.5 mm. In another embodiment, the length of the fibers is about 1.0 mm or less.

In another embodiment, the diameter or width of the fibers are, for example, not more than about 500 microns, not more than about 50 microns, or not more than about 25 microns. In still another embodiment, the diameter or width of the fibers can be from about 10 microns to about 25 microns or from about 15 microns to about 20 microns.

In another embodiment, the resorbable fibers can comprise homopolymers or copolymers of monomers selected from the group consisting of L-lactide; L-lactic acid; D-lactide; D-lactic acid; D,L-lactide; glycolide; α-hydroxybutyric acid; α-hydroxyvaleric acid; α-hydroxyacetic acid; α-hydroxycaproic acid; α-hydroxyheptanoic acid; α-hydroxydecanoic acid; α-hydroxymyristic acid; α-hydroxyoctanoic acid; α-hydroxystearic acid; hydroxybutyrate; hydroxyvalerate; β-propiolactide; α-propiolactic acid; γ-caprolactone; β-caprolactone; γ-butyrolactone; pivalolactone; tetramethylglycolide; tetramethylglycolic acid; dimethylglycolic acid; trimethylene carbonate; dioxanone; those monomers that form liquid crystal (co)polymers; those monomers that form cellulose; those monomers that form cellulose acetate; those monomers that form carboxymethylcellulose; those monomers that form hydroxypropylmethyl-cellulose; polyurethane precursors comprising macrodiols selected from the group consisting of polycaprolactone, poly(ethylene oxide), poly(ethylene glycol), poly(ethylene adipate), poly(butylene oxide), and a mixture thereof, isocyanate-functional compounds selected from the group consisting of hexamethylene diisocyanate, isophorone diisocyanate, cyclohexane diisocyanate, hydrogenated methylene diphenylene diisocyanate, and a mixture thereof, and chain extenders selected from the group consisting of ethylenediamine, 1,4-butanediol, 1,2-butanediol, 2-amino-1-butanol, thiodiethylene diol, 2-mercaptoethyl ether, 3-hexyne-2,5-diol, citric acid, and a mixture thereof; collagen, alginates (e.g., sodium or calcium alginate), polysaccharides such as chitin and chitosan, poly(propylene fumarate); and any mixture thereof.

In still another embodiment, the resorbable fibers comprise a poly(L-lactide) (co)polymer, a poly(D,L-lactide) (co)polymer, a polyglycolide (co)polymer, a polycaprolactone (co) polymer, a poly(tetramethylglycolic acid) (co)polymer, a polydioxanone (co) polymer, a polyhydroxybutyrate (co) polymer, a polyhydroxyvalerate (co)polymer, a poly(L-lactide-co-glycolide) copolymer, a poly(glycolide-co-trimethylene carbonate) copolymer, a poly(glycolide-co-caprolactone) copolymer, a poly(glycolide-co-dioxanone-co-trimethylene carbonate) copolymer, a poly(tetramethylglycolic acid-co-dioxanone-co-trimethylene carbonate) copolymer, a poly(glycolide-co-caprolactone-co-L-lactide-co-trimethylene carbonate) copolymer, a poly(hydroxybutyrate-co-hydroxyvalerate) copolymer, a liquid crystal (co) polymer, a combination thereof, or a copolymer thereof. Preferably, the resorbable fibers comprise a poly(L-lactide-co-glycolide) copolymer.

In one embodiment, the poly(L-lactide-co-glycolide) copolymer comprises at least about 15% of glycolide repeat units and at least about 15% of L-lactic acid repeat units. In another embodiment, the poly(L-lactide-co-glycolide) copolymer comprises about 82% of glycolide repeat units and about 18% of L-lactic acid repeat units. In another embodiment, the poly(L-lactide-co-glycolide) copolymer comprises about 18% of glycolide repeat units and about 82% of L-lactic acid repeat units.

In one preferred embodiment, the resorbable fibers can include or are composed of poly-L-lactide (e.g., PLLA) homopolymers, polyglycolide (PGA) homopolymers, or copolymers thereof with each other or with one or more other biodegradable or biocompatible monomers. For example, poly(L-lactide-co-glycolide) copolymers contain: L-lactide dimer or L-lactic acid monomer repeat units; and glycolide dimer or glycolic acid repeat units in the copolymer. While the repeat units are similar for polymers formed from monomers or dimers, the (co)polymer name usually depends upon the polymerization process used to form these copolymers. However, as used herein, reference to (co)polymers of lactide, glycolide, or lactide-co-glycolide, for example, should be understood to refer to (co)polymers having the basic repeat unit structure, regardless of the nature of the compound (monomer or dimer) from which they were formed. Poly(L-lactide-co-glycolide) copolymers are a preferred resorbable fiber according to the invention.

When poly(L-lactide-co-glycolide) copolymer fibers are used in the composition according to the invention, it is preferable that the copolymers contain at least 11% of each of the L-lactide and glycolide component repeat units, preferably at least about 13%, more preferably at least about 15%, for example at least about 17%. Thus, preferred poly(L-lactide-co-glycolide) copolymer fibers according to the invention can contain from 11% to 89% L-lactide repeat units and from 89% to 11% glycolide units, preferably from about 13% to about 87% L-lactide repeat units and from about 87% to about 13% glycolide units, more preferably from about 15% to about 85% L-lactide repeat units and from about 85% to about 15% glycolide units, for example from about 17% to about 83% L-lactide repeat units and from about 83% to about 17% glycolide units. In one embodiment, the aforementioned percentage represent weight percentages of the component repeat units. In another embodiment, the aforementioned percentages represent mole percentages of the component repeat units. In a preferred embodiment, the poly(L-lactide-co-glycolide) copolymer fibers contain about 82% by weight of the lactide component and about 18% by weight of the glycolide component.

In an alternate preferred embodiment, when poly(L-lactide-co-glycolide) copolymer fibers are used in the composition according to the invention, the copolymers can contain from about 2% to about 40% of the L-lactide component repeat units or from about 2% to about 40% of the glycolide component repeat units, for example from about 5% to about 30% of the L-lactide component repeat units or from about 5% to about 30% of the glycolide component repeat units. In another alternate preferred embodiment, when poly(L-lactide-co-glycolide) copolymer fibers are used in the composition according to the invention, the copolymers can contain from about 40% to about 60% of each of the L-lactide and glycolide component repeat units. In one embodiment, the aforementioned percentages represent weight percentages of the component repeat units. In another embodiment, the aforementioned percentages represent mole percentages of the component repeat units.

In one embodiment, the implantable composition according to the invention contains a distribution of copolymer fiber compositions, either of the same basic chemical make-up or of a variety of different chemical make-ups, which can advantageously allow tailoring of biological properties and/or responses related to bone void/defect healing/regeneration, e.g., angiogenesis, bone ingrowth, bone remodeling, collagen formation, in vivo degradation, in vivo loss of mechanical properties, or the like, or a combination thereof.

In an alternate embodiment, a third type of repeat unit can be present in the poly(L-lactide-co-glycolide) copolymers according to the present invention, e.g., D-lactide dimer, D,L-lactide (or mesh-lactide) dimer, the ring-opened structure of ε-caprolactone (or pentamethylene carboxylate ester) monomer, or D-lactic acid monomer, again depending upon the polymerization process used to form these copolymers.

Also, alternately, other types of resorbable, biodegradable, and/or biocompatible monomers or dimers can optionally be present as repeat units in the copolymers according to the present invention. Such suitable other monomers or dimers include, for example, but are not limited to, α-hydroxy acids, such as α-hydroxybutyric acid, α-hydroxyvaleric acid, α-hydroxyacetic acid, α-hydroxycaproic acid, α-hydroxyheptanoic acid, α-hydroxydecanoic acid, α-hydroxymyristic acid, α-hydroxyoctanoic acid, α-hydroxystearic acid, or the like, adducts thereof (e.g., hydroxybutyrate, hydroxyvalerate, etc.), dehydration product dimers thereof, or derivatives thereof, or mixtures thereof; lactide or lactic acid adducts or derivatives, such as β-propiolactide or β-propiolactic acid, or mixtures thereof; other cyclic, linear, or branched esters, such as γ-caprolactone, β-caprolactone, γ-butyrolactone, pivalolactone, or the like, glycolide or glycolic acid adducts or derivatives, such as tetramethylglycolide, tetramethylglycolic acid, dimethylglycolic acid, or the like, or mixtures thereof; carbonates such as trimethylene carbonate; cellulosic repeat units including but not limited to, e.g., cellulose, cellulose acetate, carboxymethylcellulose, hydroxypropylmethyl-cellulose, or the like; polyurethane precursors comprising macrodiols selected from the group consisting of polycaprolactone, poly(ethylene oxide), poly(ethylene glycol), poly(ethylene adipate), poly(butylene oxide), and a mixture thereof, isocyanate-functional compounds selected from the group consisting of hexamethylene diisocyanate, isophorone diisocyanate, cyclohexane diisocyanate, hydrogenated methylene diphenylene diisocyanate, and a mixture thereof, and chain extenders selected from the group consisting of ethylenediamine, 1,4-butanediol, 1,2-butanediol, 2-amino-1-butanol, thiodiethylene diol, 2-mercaptoethyl ether, 3-hexyne-2,5-diol, citric acid, and a mixture thereof; collagen, alginates (e.g., sodium or calcium alginate), chitin, chitosan, poly(propylene fumarate); or combinations or mixtures thereof.

When present, the amount of the third and/or other types of optional resorbable and/or biocompatible monomers or dimers in the poly(L-lactide-co-glycolide) copolymer fibers according to the invention can, in one embodiment, be less than about 5 mol %, for example less than about 2 mol %, or alternately from about 0.1 mol % to about 1.5 mol % or from about 1 mol % to 5 mol % based on the total amount of monomer units. In alternate embodiments, the amount of the third and/or other types of optional resorbable and/or biocompatible monomers or dimers in the poly(L-lactide-co-glycolide) copolymer fibers according to the invention can be from about 5 mol % to about 20 mol % based on the total amount of monomer units.

Additionally or alternately, the fibers according to the invention can contain or be formed from resorbable homopolymers or copolymers of any one or more of the monomers/dimers mentioned above. For example, the poly(L-lactide-co-glycolide) copolymers according to the invention preferably exhibit as close to a statistically random distribution of monomeric or dimeric repeat units as possible, taking into consideration the possible effect of the differences in reactivity ratios between the respective monomers or dimers. While copolymers of two or more resorbable and/or biocompatible monomers are typically desired to be random, there can be some alternating, blocky, tacticity, or other non-random character in arrangement of the repeat units of the copolymer fibers according to the present invention that may stem from such reactivity ratio differences. In an alternate embodiment, the copolymers can include block copolymers, multiblock copolymers, alternating copolymers, or the like, or combinations thereof.

In another embodiment, the fiber components can be non-resorbable and/or but still somewhat biodegradable (e.g., yet without being severely cytotoxic; i.e., at least being sufficiently biocompatible). Examples of suitable non-resorbable and/or still somewhat biodegradable fiber materials can include, but are not limited to polyester fibers such as polycaprolactones, poly(ethylene terephthalate), poly(butylene terephthalate), and the like, as well as combinations or copolymers thereof; bioactive glass fibers; aromatic polyamide fibers, e.g., aramid fibers such as those commercially available under the tradename KEVLAR; aliphatic polyamide fibers such as nylon 6,6, nylon 6,9, nylon 6,10, nylon 6,12, nylon 6, and the like, as well as combinations or copolymers thereof; polyurethane fibers, e.g., polyurethaneureas such as polyetherurethaneureas, polyesterurethaneureas, polycarbonateurethaneureas, and the like, polyetherurethanes, polyesterurethanes, polycarbonateurethanes, polyesterurethaneamides, and the like, as well as combinations or copolymers thereof; polyether fibers, e.g., poly(alkylene oxide)s or poly(alkylene glycol)s such as poly(ethylene oxide), poly(ethylene glycol), and the like, as well as combinations or copolymers thereof, poly(ether ether ketone)s, and the like, as well as combinations or copolymers thereof; polycarbonate fibers; polyimide fibers; poly(ethyleneimine) fibers; polydioxanone fibers; liquid crystal (co)polymers such as those commercially available from Celanese under the tradename VECTRAN; and the like; as well as copolymer fibers having repeat units of any of the preceding polymer or copolymer fibers listed above. Other alternate types of non-resorbable fibers can include, but are not limited to, carbon fibers; fiberglass fibers; metal fibers such as stainless steel fibers, titanium fibers, metal alloy fibers, and the like, and any combination thereof; and the like; and combinations thereof.

The resorbable (co)polymers that can make up the fibers of the present invention can advantageously be made by polymerizing the various types of acid dimers (e.g., L-lactide, glycolide, or other optional dehydration product acid dimers such as D-lactide, D,L-lactide, and the like, or combinations thereof), along with any desired cyclic ester monomers, if present. Alternatively, the resorbable (co)polymers can be made by polymerizing only monomeric forms of the biocompatible acids mentioned above (e.g., L-lactic acid, glycolic acid, or other optional acid monomers such as D-lactic acid and the like, or combinations thereof) and of the desired cyclic ester monomers, if present. In yet another alternative embodiment, the resorbable (co)polymers can be made from some mixture of monomeric (e.g., L-lactic acid, glycolic acid, or other optional acid monomers such as D-lactic acid and the like, or combinations thereof) and dimeric forms (e.g., L-lactide, glycolide, or other optional dehydration product acid dimers such as D-lactide, D,L-lactide, and the like, or combinations thereof) of the resorbable components mentioned above and of the desired cyclic and/or dimeric esters, if present.

For instance, any polymerization method capable of forming a polylactide or polyglycolide copolymer can be utilized to make the poly(L-lactide-co-glycolide) copolymers, particularly any method capable of forming the copolymer such that the biodegradation or resorbability and the mechanical properties (e.g., before and during implantation) are sufficient for the requirements of the application for which the copolymer is to be used. For example, one such polymerization method can be found in U.S. Pat. No. 6,096,855, the entire disclosure of which is incorporated herein by reference hereto. Other examples of copolymerizations method for producing poly(D,L-lactide-co-glycolide) and other random copolymers of resorbable materials are disclosed in U.S. Pat. No. 4,157,437 and International Publication No. WO 97/36553, the entire disclosures of which are also incorporated herein by reference hereto.

Advantageously, the (co)polymers from which fibers according to the invention can be formed, whatever their method of polymerization, must have a sufficient molecular weight to be able to perform (e.g., mechanically) in the desired application. Generally, a sufficiently high molecular weight can be obtained by polymerizing substantially all (i.e., preferably at least about 98 mol %, more preferably at least about 99 mol %, most preferably at least about 99.5 mol %) of the monomeric and/or dimeric copolymer substituents. As used herein, the term "molecular weight" should be understood to mean extent of polymerization, or number or weight average of monomeric or dimeric units in the copolymer chains. Molecular weight, as used herein, can be approximated by a number of known methods, e.g., such as by gel permeation or size exclusion chromatography (GPC or SEC), by inherent or intrinsic viscosity analysis (I.V.), or by an equivalent scientific technique through which a correlation can be made to estimate copolymer molecular weight.

When measured by GPC or SEC against polystyrene standards, the (co)polymers according to the invention (before being processed or fabricated into fibers) can, in one embodiment, exhibit a number average molecular weight of at least about 75,000 grams/mole, for example from about 150,000 grams/mole to about 1,000,000 grams/mole or from about 250,000 grams/mole to about 900,000 grams/mole. Such measurements can, in another embodiment, also yield a weight average molecular weight of at least about 125,000 grams/mole, for example at least about 250,000 grams/mole or from about 400,000 grams/mole to about 2,500,000 grams/mole. Alternately, in some embodiments, the number average molecular weight can be between about 16,000 grams/mole and about 75,000 grams/mole or between about 18,000 grams/mole and about 50,000 grams/mole, and the number average molecular weight can be between about 50,000 grams/mole and about 150,000 grams/mole or between about 60,000 grams/mole and about 120,000 grams/mole. In another embodiment, such measurements can also show a polydispersity (i.e., a ratio of weight average molecular weight to number average molecular weight) from about 1.3 to about 3.5, for example from about 1.6 to about 2.8 or from about 1.85 to about 2.5. However, the desired application for which the fibers will be used should generally determine the acceptable range of molecular weight values, e.g., a copolymer used for drug delivery, maxillofacial implant, or other application in which enhanced biodegradation or resorbability is paramount, may be preferred to exhibit number average and/or weight average molecular weights in a lower region of, or even below, the ranges listed above, whereas a copolymer used in a pin, rod, anchor, staple, or other mechanically-intensive and/or load-bearing application may be preferred to exhibit number average and/or weight average molecular weights in an intermediate or upper region of, or even above, the ranges listed above.

When measured for I.V. at a concentration of about 0.1% w/v in chloroform, the (co)polymers according to the invention (before being processed or fabricated into fibers) can, in one embodiment, exhibit an inherent viscosity of at least about 1.0 dL/g, for example from about 2.5 dL/g to about 8 dL/g, from about 3 dL/g to about 7 dL/g or from about 4 dL/g to about 6.5 dL/g. In another embodiment, the inherent viscosity of the poly(L-lactide-co-glycolide) copolymer of the invention can be greater than about 4.5 dL/g. However, the desired application for which the fibers will be used should generally determine the acceptable range of inherent viscosity values, e.g., a copolymer used for drug delivery, maxillofacial implant, or other application in which enhanced biodegradation or resorbability is paramount, may be preferred to exhibit lower inherent or intrinsic viscosities than those listed above, whereas fibers used in a composite for a pin, rod, anchor, staple, or other mechanically-intensive and/or load-bearing application may be preferred to exhibit inherent or intrinsic viscosities within, or even above, those listed above.

The fibers according to the invention can have a low moisture (or water) content (i.e., before being combined with the calcium salt-containing component), for example, not more than about 1.5% by weight or not more than about 1% by weight. In one embodiment, the moisture or water content can be not more than about 500 ppm, for example not more than about 250 ppm or not more than about 150 ppm. In other embodiments, the moisture or water content of fibers according to the invention can be not more than about 200 ppm or not more than about 100 ppm.

In some circumstances, the fibers according to the invention can be subject to a drying and/or volatile organic compound (VOC) removal step, in order to remove water, organic solvent(s), unreacted monomer/dimer, or other low molecular weight and/or volatile impurities or compounds that can be present in the (co)polymer fibers. This drying/removal step can include, but is not limited to, introduction of a relatively-dry, inert gas (e.g., such as dry nitrogen, argon, or the like, or a mixture containing such a gas), application of a vacuum (e.g., such that the pressure is not more than about 10 Torr, for example more than about 5 Torr or not more than about 1 Torr), application of an increased temperature (e.g., of at least about 50° C., for example at least about 65° C. such as from about 70° C. to about 120° C., and also preferably, provided that the copolymer is at least partially crystalline, that the increased temperature is not greater than about 5° C. below its melting temperature, for example not greater than about 10° C. below its melting temperature), or any combination thereof. This drying/removal step is generally undertaken for a period of time sufficient to render the moisture content within acceptable or preferred limits. When performed, the step can advantageously include a combination of application of increased temperature and application of a vacuum and occurs for at least about 4 hours, for example for at least about 12 hours, or alternately for not more than about 24 hours or from about 16 hours to about 20 hours.

The (co)polymer fibers according to the present invention can exhibit a wide range of degrees of crystallinity, with preferable values depending upon the desired application for which they are to be used. In one embodiment, the fibers of the invention are semicrystalline and can exhibit a degree of crystallinity from about 15% to about 30%, for example from about 20% to about 30% such as from about 20% to about 26%. In another embodiment, the fibers of the invention can exhibit a degree of crystallinity of less than about 15%. In an alternate embodiment, the fibers of the invention can exhibit a degree of crystallinity from about 15% to about 50%. In other alternate embodiments, the fibers of the invention can exhibit a degree of crystallinity of less than about 10%, less than about 5%, less than about 1%, or can exhibit substantially no crystallinity (i.e., less than about 0.5%, preferably less than about 0.1%, or at any rate not quantitatively detectable by one or more experimental methods). The "degree of crystallinity" can be measured by a number of well-known experimental techniques and, when the term is used herein, reflects the relative proportion, by volume, cross-sectional area, or linear path through a sample, of crystalline regions in comparison to non-crystalline or amorphous regions of the fibers. Suitable experimental techniques to measure degree of crystallinity include, but are not limited to, differential scanning calorimetry (DSC), x-ray scattering or diffraction methods (e.g., XRD, WAXD, WAXS, etc.), or the like.

The (co)polymer fibers according to the present invention can also exhibit a wide range of degrees of crystalline perfection (or crystalline imperfection), again with preferable values depending upon the desired application for which they are to be used. The degree of crystalline perfection or imperfection can be measured, for example, by DSC or another well-known experimental technique and can be referred to herein in terms of a heat of fusion ($\Delta H_f$), which represents the relative perfection or imperfection of the crystals of the copolymer in terms of the amount of energy per unit of material (e.g., in Joules per gram, J/g, or millijoules per milligram, mJ/mg) required to melt, or de-crystallize, the crystals of the copolymer. In one embodiment, the fibers of the invention are semicrystalline and can exhibit a heat of fusion of less than about 50 J/g, for example less than about 30 J/g or less than about 25 J/g. In another embodiment, the fibers of the invention can exhibit a heat of fusion from about 50 J/g to about 70 J/g. In alternate embodiments, the fibers of the invention can exhibit a heat of fusion of from about 0.5 J/g to about 15 J/g, from about 0.1 J/g to about 10 J/g, from about 15 J/g to about 25 J/g, or can exhibit substantially no heat of fusion (i.e., less than about 0.1 J/g, or at any rate not quantitatively detectable by one or more experimental methods).

Melting temperatures and glass transition temperatures for the (co)polymer fibers according to the present invention can also vary widely, with preferable values depending upon the desired application for which they are to be used. Melting and glass transition temperatures can be measured, for example, by DSC or another well-known experimental technique, and are generally dependent upon the rate at which temperature is increased or decreased. Standard DSC tests are performed with temperature changing at a rate of about 5° C./min to about 20° C./min, particularly at about 10° C./min. When present, the melting temperature of the fibers of the present invention, as measured by standard DSC tests, can, in one embodiment, be between about 90° C. and about 165° C. for example from about 110° C. to about 155° C. or from about 130° C. to about 150° C. The glass transition temperatures of the fibers of the present invention, as measured by standard DSC tests, can, in another embodiment, be between about 30° C. and about 100° C., for example between about 40° C. and about 60° C.

While preferable values can vary widely, depending inter alia upon the desired application for which they are to be used and the process by which they are formed into articles or devices for said applications, the (co)polymer fibers according to the present invention can, in one embodiment, exhibit mechanical properties that can vary as follows:

| MECHANICAL PROPERTY | RANGE OF VALUES |
| --- | --- |
| Flexural Modulus | about 3 to about 14 GPa |
| Flexural Strength | about 100 to about 200 MPa |
| Tensile Modulus (secant at 0.2% strain) | about 5 to about 9 GPa |
| Tensile Strength | about 50 to about 175 MPa |
| Shear Strength | about 90 to about 175 MPa |

As the fibers and/or compositions according to the invention have utility in implantations and in vivo applications, it may be desirable to sterilize such fibers and/or composites to minimize in vivo response, e.g., from infection, foreign body rejection, or the like. Because the resorbable fibers of the invention are degradable in the presence of water, sterilization methods other than autoclaving are particularly appropriate. Such sterilization can include, but are not limited to, exposure to ethylene oxide, exposure to γ-radiation, exposure to an electron beam source, exposure to a cold (or at least low-temperature) plasma source, or a combination thereof. The sterilization process, depending upon the exposure dose and duration, may be one possible way to introduce branching, grafting, or crosslinking to the copolymer fibers of the present invention. The sterilization process, depending upon the exposure dose and duration, can additionally or alternately alter the surface chemistry and/or electronic structure, which may increase or decrease the compatibility between the fiber and the matrix (e.g., through fiber wetting, reactive bonding, or the like).

Single or multiple doses to these means of sterilization can be performed on the copolymers, articles, or devices according to the invention in an amount, or in amounts, sufficient to prevent, inhibit, or curtail in vivo response. In one preferred embodiment, the sterilization includes a single dose exposure to γ-radiation or ethylene oxide. In another preferred embodiment, the sterilization includes a single dose exposure of the poly(L-lactide-co-glycolide) copolymers or devices according to the invention to γ-radiation of 25 kGy.

(Co)polymer fibers and/or compositions containing them tend to exhibit complete in vivo or in vitro resorption from about 1 month to about 2.5 years, for example from about 2 months to about 2 years. As used herein, "complete resorption" refers to the situation where, upon visual inspection, there is either no evidence of (co)polymeric material at the site of implantation, or where, upon analysis of a sample of the implantation site of the degraded copolymer, there is an absence of oligomeric material resultant from degradation of the (co)polymer that has a number average molecular weight of more than about 1,000 grams/mole or not more than about 500 grams/mole. In another embodiment, the fibers and/or compositions according to the invention should typically retain at least a portion of their mechanical properties after implantation in vivo or after exposure to a phosphate buffered saline (PBS) solution having a pH of about 7.4 (±0.2) at a temperature of about 37° C. (±1° C.).

The dimensions of the fiber material, e.g., the aspect ratio, is also an important consideration. As used herein, the term "aspect ratio," at least in reference to the fibers according to the invention, should be understood to refer preferably to length-over-diameter for relatively cylindrical fibers (relatively circular cross-section), and alternately to length-over-longest width for prismatic, irregular, or other non-cylindrical fibers (having predominantly non-circular cross-sections).

Fibers according to the invention can advantageously have an aspect ratio from about 50:1 to about 1000:1, from about 50:1 to about 950:1, from about 50:1 to about 750:1, from about 50:1 to about 600:1, from about 50:1 to about 350:1, from about 50:1 to about 200:1, from about 50:1 to about 100:1, or from about 50:1 to about 75:1. In a more preferred embodiment, the aspect ratio is about 62:1.

In one embodiment, the implantable composition according to the invention contains a distribution of fiber aspect ratios, either completely within the recited ranges or partially within the recited ranges and partially outside the recited ranges (above and/or below), which may advantageously allow tailoring of biological properties and/or responses related to bone void/defect healing/regeneration, e.g., angiogenesis, bone ingrowth, bone remodeling, collagen formation, in vivo degradation, in vivo loss of mechanical properties, or the like, or a combination thereof.

Fibers useful in the composition of the present invention generally have a length of about 0.1 mm to about 15 mm, preferably about 0.1 mm to about 8.5 mm. Applicants have found that shorter length fibers resist phase separation (e.g., fiber settling in aqueous medium) and are preferred in injectable compositions. When used with an injectable composition, the fibers preferably have a length of about 0.1 mm to about 1.5 mm, more preferably of about 0.25 mm to about 1.25 mm, most preferably about 1 mm.

The fibers generally have a diameter or width of at least about 5 microns to 5 about 500 microns, from about 10 microns to about 500 microns, from about 10 microns to about 100 microns, from about 10 microns to about 25 microns, or from about 15 microns to about 25 microns. In a preferred embodiment, the width of the fibers is about 16 microns. Without being bound by theory, it is believed that fibers having diameters or widths wider than this may create difficulties in mixing with the calcium salt-containing component and/or in uniformity of the dispersion of the fibers in a calcium salt-containing component matrix. However, it is also possible that fibers having larger diameters or widths may be effective when longer fibers are utilized (again, the effects of fiber aspect ratio on the properties of the composite are described above) or in overcoming difficulties in mixing.

In one embodiment, fibers having larger diameters or widths could be created, e.g., by aggregating, braiding, bundling, or the like (hereinafter bundling, for convenience and without intent to unduly limit) fibers having smaller diameters or widths into fiber bundles. For example, larger diameter fibers or braided bundles of fibers can be added to increase cellular ingrowth and accelerate degradation time. The bundles of fibers, when used, can be from about 100 microns to about 500 microns.

In one embodiment, the implantable composition according to the invention contains a distribution of fiber lengths and/or diameters/widths, which can advantageously allow tailoring of biological properties and/or responses related to bone void/defect healing/regeneration, e.g., angiogenesis, bone ingrowth, bone remodeling, collagen formation, in vivo degradation, in vivo loss of mechanical properties, or the like, or a combination thereof.

The (co)polymer fibers according to the invention (e.g., resorbable fibers such as poly(L-lactide-co-glycolide)) are typically linear or only lightly branched, grafted, or crosslinked (e.g., at least about 98%, preferably at least about 99%, of the monomers or dimers are located on a linear polymer backbone and not in a branch or graft side chain or in a crosslink connector chain).

The geometry of the ends of the fibers can also have an important impact on the properties of the composite material. Typically, because fibers are often fabricated by a continuous process, it can be necessary to cut continuous fibers in order to get fibers of a desired length (e.g., tailored to the diameter thereof, based on the aspect ratio constraints described herein). In such a case, the fiber ends are typically sliced, broken, etc., and can be thought of as essentially flat and/or featureless. However, fibers having features on the ends can have advantageous effects on the properties of the fibers in the composition according to the invention. For example, beads or balls can be formed on the ends of fibers or groups of fibers, e.g., by heating one or more of the ends of the fiber(s) such that the end(s) melt or burn and thus (each) form a hemispherical end bead. For instance, about seven cylindrical poly(L-lactide-co-glycolide) copolymers (specifically, 18/82 L/G), having fiber diameters of about 15 to about 20 microns and grouped in a 2-3-2 array (i.e., a hexagonal arrangement with one fiber in the middle) most closely approximating a multifibrillar cylinder, were heated to a temperature of at least about 55° C., for example at least about 75° C., or at least about 100° C., on each end to form a ball or bead, thus joining the seven-fiber construct to form a multifibrillar fiber having an effective diameter of about 45 to about 60 microns, while maintaining a similar length. Other types of alterations to the fiber ends can also be accomplished, e.g., to form dogbone-shaped short fibers, such as described in the article of Zhu et al., "Bone-Shaped Short Fiber Composites—An Overview," *Mat. Sci. & Eng.*, 2002, A326, 208-227, the entire disclosure of which is hereby incorporated by express reference hereto.

When the fiber ends have been altered or have a shape other than substantially flat and/or featureless (as is typical of most chopped fibers), the aspect ratio constraints mentioned above can be relaxed, particularly on the low end of the ratio. Therefore, where the fiber ends have been altered or have a shape other than substantially flat and/or featureless, for example where ends of the fibers have shapes of beads, balls, dogbone shapes or dumbbell shapes, etc., the aspect ratio range can remain the same or advantageously change to be from about 50:1 to about 500:1, for example from about 75:1 to about 500:1, such as from about 100:1 to about 250:1. In cases where the fiber ends have been altered or have a shape other than substantially flat and/or featureless, the aspect ratio can be calculated using the diameter or width of the fibers away from the ends.

Similarly, when the fibers have been textured to increase pullout resistance (e.g., kinking or crimping the fiber), the aspect ratio can be calculated using the diameter or width of the fibers in the stretched form.

Whether altered at their ends or unaltered, the surface of the fibers according to the invention can optionally be treated to change their chemical structure, their physical structure, their mechanical structure, their electronic structure, their magnetic structure, their adhesion properties, or some combination thereof. Examples of such treatment can include, but is not limited to, placement of regular or irregular ribs on the fiber surface (e.g., such as found on rebar), kinking or crimping the fiber, chemically adhering calcium ions or components to the fiber surface to form a calcium-rich surface, chemically treating the fibers (e.g., with strong acid or strong base), physically treating the fibers (e.g., corona discharge or plasma discharge), electronically altering the charge on the fiber surface, or the like, or a combination thereof.

When injected, the composition of the invention advantageously comprises a flow additive. Without being limited by theory, Applicants believe that the flow additive increases the viscosity of the injectable composition, prevents or delays phase separation, and enhances the flowability of the injectable composition through, e.g., a syringe needle having a gauge from about 12 to about 18 with a maximum injection pressure of not more than about 40 pounds. In preferred embodiments, the viscosity of the injectable composition is from about 1 cPs to about 500 cPs, preferably from about 1 cPs to about 300 cPs.

The flow additive, when used, is typically present in an amount from about 0.05% to about 5%, from about 0.1% to about 2.5%, or from about 0.25% to about 1% by weight of solid components of the composition. In one embodiment, the flow additive, when used, is present in amount of about 0.22% by weight of solid components and liquid components of the composition.

Non-limiting examples of useful flow additives include hyaluronic acid, a hyaluronate salt, a sodium phosphate salt, or a combination thereof. In a preferred embodiment, the flow additive comprises sodium hyaluronate and preferably consists essentially of sodium hyaluronate.

The amount of fibers that can be contained in the composition according to the invention can advantageously be from about 0.1% to about 20% by weight, preferably from about 1% to about 10%, for example from about 1% to about 8%, from about 1% to about 5%, from about 1% to about 3%, or from about 1% to about 2.5% based on the weight of the solid components. Although fiber loadings of less than about 1% may have some effect on the properties of the composition, it is generally desirable for optimal effectiveness to have fiber loadings of about 1% by weight or more to attain the best improvement in properties of the composite material over that of the calcium salt-containing component alone. In a preferred embodiment, the compositions contains about 3% by weight of fiber based on the weight of the solid components. In another embodiment, the compositions contains about 3% by weight of fiber based on the weight of the solid components and liquid components.

The combination of fibers with the calcium salt-containing component in the composition according to the invention can advantageously cause increases in certain mechanical properties (e.g., flexural strength, screw pullout strength, flexural toughness, fracture toughness, flexural fatigue life, strain-to-break, fracture stress, ultimate tensile strength, tensile strength, tensile modulus, tensile toughness, and the like, and combinations thereof) of the composition, as compared to the same mechanical properties of the calcium salt-containing component alone. In one embodiment, the presence of fibers in the composite results in a flexural strength increase of at least about 10%, preferably at least about 20%, more preferably at least about 50%, for example at least about 100%, at least about 200%, or at least about 350%. In this embodiment, the presence of fibers in the composite can generally result in a flexural strength increase of less than about 1000%, typically less than about 900%, for example not more than about 800% or not more than about 700%. Testing of flexural strength can advantageously be done according to ASTM C-1161 standard testing methods. In another embodiment, the presence of fibers in the composite results in an increase in the flexural toughness (as used herein, "flexural toughness" is defined as the area under the flexural load/stress vs. displacement/strain curve in a flexural strength test, e.g., a test done according to ASTM C-1161 standard testing methods) of at least about 25-fold, preferably at least about 35-fold, for example at least about 50-fold, at least about 60-fold, at least about 75-fold, or at least about 100-fold. In still another embodiment, presence of fibers in the composite results in a screw pullout strength increase of at least about 50%, preferably at least about 75%, for example at least about 100%, at least about 125%, at least about 150%, or at least about 200%. In this embodiment, the presence of fibers in the composite can generally result in a screw pullout strength increase of less than about 900%, typically less than about 800%, for example not more than about 700% or not more than about 600%. Screw pullout testing can advantageously be done by measuring the maximum load necessary to pull out a 25 mm #3 screw or a 3 mm-long screw in tension at an angle from about 30 to about 45 degrees to the normal to that surface from a drilled and tapped hole in the middle of the 8×50 mm rectangular side of 6×8×50 mm molded samples, using a load cell having a maximum capacity of 100-1000 N at a head speed of about 0.5 in/min.

In some embodiments, it is preferable that the advantageous increases in certain mechanical properties by the introduction of fibers is not accompanied by large decreases in other mechanical properties (e.g., compressive strength, flexural strength, flexural work of fracture, and the like) crucial to the performance of the compositions according to the invention in their (in vivo) applications. In one embodiment, the presence of fibers in the composite can generally result in a compressive strength decrease of less than about 20%, occasionally less than about 10%, for example not more than about 8% or not more than about 5%. Compression testing can advantageously be done by INSTRON testing of cylindrical samples having a cross-section with a diameter of about 6 mm and a length of about 12 mm at a crosshead speed of about 0.1 inches per minute.

In one embodiment, the compressive strength of the fiber-reinforced composition without continuous fiber reinforcement is at least about 15 MPa; in another embodiment, at least about 35 MPa. In one embodiment, the compressive strength of the fiber-reinforced composition without continuous fiber reinforcement is from about 15 to about 80 MPa; in another embodiment, from about 20 to about 60 MPa; and in another embodiment, about 35-40 MPa.

In one embodiment, the flexural strength of the fiber-reinforced composition without continuous fiber reinforcement is at least about 6 MPa; in another embodiment, at least about 8 MPa. In one embodiment, the flexural strength of the fiber-reinforced composition without continuous fiber reinforcement is from about 6 to about 12 MPa; in another embodiment, from about 7 to about 10 MPa; and in another embodiment, about 8 MPa.

In one embodiment, the flexural work of fracture of the fiber-reinforced composition without continuous fiber reinforcement is at least about 400 J/m$^2$; in another embodiment, at least about 900 J/m$^2$. In one embodiment, the flexural work of fracture of the fiber-reinforced composition without continuous fiber reinforcement is from about 400 to about 2400 J/m$^2$; in another embodiment, from about 750 to about 1500 J/m$^2$; and in another embodiment, from about 900 to about 1200 J/m$^2$. Flexural work of fracture is a measurement of toughness that may be measured by any desired method as known to one skilled in the art.

Besides bulk mechanical properties, another advantage of using fiber-reinforced compositions according to the invention, particularly in craniofacial applications, is their reduced brittleness, as compared to non-fiber-reinforced calcium phosphate-containing compositions, and their increased viscoelastic stability and mechanical/structural integrity, primarily in resistance to or elimination of catastrophic implant failure, but also in areas such as in resistance to or elimination of crack propagation, resistance to or elimination of crack formation, resistance to or elimination of void formation, or the like, or a combination thereof, all of which can occur, e.g., as a result of dural motion, particularly micromotions or pulsations. These motions and/or micromotions can be especially pronounced during the setting process, where little mechanical strength/stability is typically provided by the calcium salt-containing component. As a result of these enhanced physical properties, the implant of the invention can be drilled or machined as required.

In order to have the capability to be formed by hand or to be injected into a unitary shape for implantation or other applications, the compositions according to the invention can also optionally contain a flow additive to enhance the flow characteristics or the moldability/deformability of the composition. Such a flow additive is typically necessary in compositions according to the invention that are formed into shapes for applications by conventional viscoelastic-liquid forming or liquid-setting means (e.g., by flow through an aperture such as injection or by unrestrained flow such as pouring, molding by hand, or the like, or a combination thereof). Such a flow additive is optional in compositions according to the invention that are formed into shapes for applications by conventional solid mechanical forming means (e.g., by packing or solid molding techniques such as molding by hand, compressing by machine, shaping by machine, or the like, or a combination thereof). In one embodiment, the flow additive can optionally be present in the composition with the calcium salt-containing component and without the fiber component.

Flow additives according to the invention can include, but are not limited to, small molecule organic compounds, polymeric/oligomeric materials, and solutions thereof that, when added to the composition (or merely to the calcium salt-containing component) change the viscosity thereof sufficiently to allow flow through, e.g., a syringe needle of about 8-gauge or greater (greater number gauges of syringe needles have smaller diameters, thus requiring lower threshold viscosity through which they may flow), preferably of about 12-gauge or greater, for example of about 14-gauge or greater, of about 15-gauge or greater, or of about 18-gauge or greater. Sufficient flow can be understood, in terms of syringe needles, to result in an injection force of not more than 50 pounds, preferably not more than 40 pounds. In one embodiment, the flow additive modifies the viscosity of the composition (or merely the calcium salt-containing component) to which it is added such that the composition is capable of flowing through a syringe needle having a gauge size from about 8 to about 18, alternately from about 8 to about 15, from about 12 to about 18, or from about 12 to about 15.

When present, the amount of flow additive that can be added to the composition (or merely to the calcium salt-containing component) can be from about 0.01% to about 1.5% by weight of the composition (or alternately by weight of the flow additive combined with the calcium salt-containing component and optionally also with the fiber component), from about 0.1% to about 1%, or from about 0.05% to about 1%. In an alternate embodiment, the amount of flow additive can be from about 1.5% to about 5% by weight of the composition (or alternately by weight of the flow additive combined with the calcium salt-containing component and optionally also with the fiber component). In a preferred embodiment, the flow additive, when used, is present in an amount of about 0.5% by weight of the composition (or alternately by weight of the flow additive combined with the calcium salt-containing component and optionally also with the fiber component).

Suitable examples of flow additives can include, but are in no way limited to, hyaluronic acid; hyaluronate salts such as sodium, potassium, lithium, or the like, or a combination thereof; alginate salts such as sodium, potassium, lithium, or the like; starch compounds, which can be present in its natural form (e.g., as extracted from one or more plants, or as purified by any method), in a destructured form, or in any number of chemically modified derivative forms (e.g., alkoxylated derivatives, esterified derivatives, ionically modified starches, oxidized starches, grafted starches, crosslinked starches, or the like, or mixtures thereof); saturated, monounsaturated, and/or polyunsaturated oils, such as those extracted or isolated from plant and/or animal sources, e.g., including, but not limited to, sunflower, safflower, peanut, castor bean, sesame, coconut, soybean, corn, canola, olive, vegetable, palmitins, stearins, oleins, and the like, or derivatives or combinations thereof; as naturally extracted, as synthesized, or as modified or processed in some way, e.g., partially or fully hydrogenated, partially or fully dehydrogenated, partially or fully saponified, partially or fully acidified, partially halogenated, or the like; a wax including, but not limited to, hydrocarbon waxes (e.g., polyolefin waxes, such as polyethylene wax, polypropylene wax, and the like, or copolymers thereof), oligoester waxes, monoester waxes, oligoether waxes, monoether waxes, and the like, or combinations thereof; as naturally extracted, as synthesized, or as modified or processed in some way, e.g., partially or fully hydrogenated, partially or fully dehydrogenated, partially or fully saponified, partially or fully acidified, partially halogenated, or the like; cellulosic compounds, e.g., including, but not limited to, native or synthetic cellulose, cotton, regenerated cellulose (e.g., rayon, cellophane, or the like), cellulose acetate, cellulose propionate, cellulose butyrate, cellulose acetate-propionate, cellulose acetate-butyrate, cellulose propionate-butyrate, cellulose nitrate, methyl cellulose, ethyl cellulose, carboxymethyl cellulose, carboxyethyl cellulose, cellulose salts, and combinations or copolymers thereof; as naturally extracted, as synthesized, or as modified or processed in some way, e.g., partially or fully esterified, partially or fully nitrated, partially or fully regenerated, partially or fully etherified, partially or fully acidified, partially or fully acid-neutralized, or the like, or combinations thereof; surface-active biomolecules or (co)polymers; poly(ethylene glycol) and/or poly(ethylene oxide) oligomers, homopolymers, or copolymers; autologous substances such as autologous bone marrow aspirates, autologous blood substances, or the like, or a combination thereof; heterologous substances such as allogeneic bone marrow aspirates, xenogenic bone marrow aspirates, allogeneic blood substances, xenogenic blood substances, or the like, or a combination thereof; or the like, or combinations thereof. In a preferred embodiment, the flow additive comprises hyaluronic acid and/or a hyaluronate salt.

In another preferred embodiment, the flow additive comprises sodium hyaluronate. In an alternate embodiment, the flow additive can include chondroitin, glucosamine, hyaluronic acid, a salt thereof; or a mixture thereof.

When the flow additive includes hyaluronic acid or a hyaluronate salt, the hyaluronic acid or hyaluronate salt can be obtained from any applicable source, e.g., including, but not limited to, bacterial fermentation; extraction and/or isolation from animal fluids (e.g., synovial fluid and the like), tissues, bones, or the like, or a combination thereof; completely or partially chemically synthesized ex vivo; or the like; or a combination thereof. The properties (e.g., molecular weight) of the hyaluronic acid or hyaluronate salt obtained from different sources can be vastly different. In one embodiment, the number average molecular weight (e.g., as measured by GPC or SEC against suitable standards such as polyethylene oxide standards) of the hyaluronic acid or hyaluronate salt can advantageously be at least about 1,000 grams/mole, preferably at least about 5,000 g/mol. In another embodiment, the number average molecular weight of the hyaluronic acid or hyaluronate salt can be from about 10,000 grams/mole to about 5,000,000 grams/mole, for example from about 50,000 grams/mole to about 3,000,000 grams/mole, from about 10,000 grams/mole to about 1,000,000 grams/mole, or from about 150,000 grams/mole to about 2,000,000 grams/mole. In another embodiment, such measurements can also yield a weight average molecular weight of at least about 1,500 grams/mole, preferably at least about 8,000 grams/mole. In yet another embodiment, such measurements can yield a weight average molecular weight from about 15,000 grams/mole to about 25,000,000 grams/mole, for example from about 75,000 grams/mole to about 10,000,000 grams/mole, from about 15,000 grams/mole to about 5,000,000 grams/mole, or from about 250,000 grams/mole to about 4,000,000 grams/mole. In still another embodiment, such measurements can show a polydispersity (i.e., a ratio of weight average molecular weight to number average molecular weight) from about 1.3 to about 10, for example from about 1.6 to about 8, from about 1.5 to about 4, from about 2 to about 7, from about 4 to about 9, or from about 1.8 to about 2.5.

When an oligomeric or (co)polymeric flow additive is used, it can be used alone or in combination with an aqueous solution, which can advantageously contain dissolved salt, pH buffer, or the like, or combinations thereof. The dissolved salt can include, but are not limited to, monosubstituted salts of monoprotic acids, monosubstituted salts of diprotic acids, disubstituted salts of diprotic acids, monosubstituted salts of triprotic acids, disubstituted salts of triprotic acids, trisubstituted salts of triprotic acids, monosubstituted salts of tetraprotic acids, disubstituted salts of tetraprotic acids, trisubstituted salts of tetraprotic acids, tetrasubstituted salts of tetraprotic acids, etc., or combinations thereof. The salt substituents can be either metallic elemental ions, organic ions such as ammonium ions, alkylammonium ions, dialkylammonium ions, trialkylammonium ions, tetraalkylammonium ions, organoammonium ions, metal-ligand complexes, or the like, or a combination thereof. Examples of suitable dissolved salts include, but are not limited to, a partially or completely substituted carbonate salt, a partially or completely substituted phosphate salt, a partially or completely substituted silicate salt, a hydroxide salt, a phosphite salt, a partially or completely substituted phosphonate salt, a nitrate salt, a partially or completely substituted sulfate salt, a partially or completely substituted sulfite salt, a halide salt such as a chloride salt, a partially or completely substituted salt of an organic or inorganic acid (e.g., as listed herein), an ammonium salt, an alkali metal salt such as a sodium or potassium salt, an alkaline earth metal salt such as a calcium salt, a transition metal salt, or the like, or a combination thereof. The pH buffer can include, but is not limited to, any one or more of the dissolved salts listed herein, along with any one or more of the acids described above, e.g., the acid corresponding to the salt.

In one preferred embodiment, the flow additive includes an aqueous solution containing a sodium phosphate, preferably $Na_2HPO_4$, for example consisting essentially of a solution of distilled water and $Na_2HPO_4$. In another preferred embodiment, the flow additive includes an aqueous solution containing $Na_2HPO_4$ and $NaH_2PO_4$, for example consisting essentially of a solution of distilled water, $Na_2HPO_4$ and $NaH_2PO_4$. In another embodiment, the flow additive includes an aqueous solution containing sodium chloride, and preferably consists essentially of saline. When the aqueous solution contains a salt or buffer component, the concentration of such component in solution can typically be from about 0.005 m to about 0.5 m, preferably from about 0.01 m to about 0.25 m. for example from about 0.01 m to about 0.1 m, from about 0.05 m to about 0.2 m, from about 0.075 m to about 0.25 m, or from about 0.15 m to about 0.25 m, with "m" connoting molality expressed in moles per kilogram of solution.

As noted above, the implant compositions can further comprise a drug or a therapeutic substance (e.g., carriers, bone ingrowth induction catalysts such as bone morphogenetic proteins, growth factors, peptides, and the like, antivirals, antibiotics, etc.), monofilament or multifilament structures, sheets, coatings, membranes (e.g., porous, microporous, resorbable, etc.), foams (e.g., open cell or closed cell), screw augmentation, cranial reconstruction, and/or combinations thereof.

The therapeutic substance can be included in the compositions according to the invention. For example, these therapeutic substances can be present in the calcium salt-containing component, in or on the fiber component, or both. The therapeutic substances can be added to the respective components, impregnated within the fibers, adhered to the surfaces of the fibers, and/or included as a controlled release formulation within one or more of the components. The therapeutic substances can include, but are in no way limited to, antibiotics, chemotherapy drugs, growth factors (particularly osteoinductive growth factors) such as bone morphogenetic proteins, endothelial growth factors, insulin growth factors, or the like, or a combination thereof.

When the therapeutic substance is an antimicrobial agent, one, and usually no more than three, usually no more than two, antimicrobial agents can be present in the implant compositions. Non-limiting examples of useful antimicrobial agents include: Antiamebics, e.g. Arsthinol, Bialamicol, Carbarsone, Cephaeline, Chlorbetamide, Chioroquine, Chlorphenoxamide, Chlortetracycline, Dehydroemetine, Dibromopropamidine, Diloxanide, Diphetarsone. Emetine, Fumagillin, Glaucarubin, Glycobiarsol, 8-Hydroxy-7-iodo-5-quinoline- sulfonic Acid, Iodochlorhydroxyquin, Iodoquinol, Paromomycin, Phanquinone, Polybenzarsol, Propamidine, Quinfamide, Secnidazole Sulfarside, Teclozan, Tetracycline, Thiocarbamizine, Thiocarbarsone, Tinidazole; Antibiotics,.e.g. Aminoglycosides (such as Amikacin, Apramycin, Arbekacin, Bambermycins, Butirosin, Dibekacin, Dihydrostreptomycin, Fortimicin(s), Gentamicin, Isepamicin, Kanamycin Micronomicin, Neomycin, Neomycin Undecylenate, Netilmicin, Paromomycin, Ribostamycin, Sisomicin, Spectinomycin, Streptomycin, Tobramycin, Trospectomycin), Amphenicols (Azidamfenicol, Chiorampheenicol, Florence, Thiamphenicol), Ansamycins (Rifamide, Rifampin, Rifamycin, Rifapentine, Rifaximin), β-Lactams (Carbacephems, Loracarbef, Carbapenems (Biapenem, Imipenem, Meropenem, Panipenem), Cephalosporins (Cefaclor, Cefadroxil, Cefamandole, Cefatrizine, Cefazedone, Cefazolin, Cefcapene, Pivoxil Cefclidin, Cefdinir, Cefditoren, Cefepime, Cefetamet, Cefixime, Cefinenoxine, Cefodizime, Cefonicid, Cefoperazone, Ceforanide, Cefotaxime, Cefotiam, Cefozopran, Cefbimizole, Cefpiramide, Cefpirome, Cefpodoxime Proxetil, Cefjrozil, Cefroxadine, Cefsulodin, Ceftazidime, Cefteram, Ceftezole, Ceftibuten, Ceftizoxime, Cefiriaxone, Cefuroxime, Cefuzonam, Cephacetrile Sodium, Cephalexin, Cephaloglycin, Cephaloridine, Cephalosporin, Cephalothin, Cephapirin Sodium, Cephradine, Pivcefalexin), Cephamycins (Cefbuperazone, Cefmetazole, Cefminox, Cefotetan, Cefoxitin), Monobactams (Aztreonam, Carumonam, Tigemonam), Oxacephens (Flomoxef, Moxalactam), Penicillins (Amdinocillin, Amdinocillin Pivoxil, Amoxicillin, Ampicillin, Apalcillin, Aspoxicillin, Azidocillin, Azlocillin, Bacampicillin, Benzylpenicillin Acid, Benzylpenicillin Sodium, Carbenicillin, Carindacillin, Clometocillin, Cloxacillin, Cyclacillin, Dicloxacillin, Epicillin, Fenbenicillin, Floxacillin, Hetacillin, Lenampicillin, Metampicillin, Methicillin Sodium, Meziocillin, Nafcillin Sodium, Oxacillin, Penamecillin, Penethamate Hydriodide, Penicillin G Benethamine, Penicillin G Benzathine, Penicillin G Benzhydrylamine, Penicillin G Calcium, Penicillin G Hydrabamine, Penicillin G Potassium, Penicillin G Procaine, Penicillin N, Penicillin O, Penicillin V, Penicillin V Benzathine, Penicillin V Hydrabamine, Penimepicycline, Phenethicillin Potassium, Piperacillin, Pivampicillin, Propicillin, Quinacillin, Sulbenicillin, Sultamicillin, Talampicillin, Temocillin, Ticarcillin), Ritipenem), Lincosamides (Clindamycin, Lincomycin), Macrolides (Azithromycin, Carbomycin, Clarithromycin, Dirithromycin, Erythromycin, Erythromycin Acistrate, Erythromycin Estolate, Erythromycin Glucoheptonate, Erythromycin Lactobionate, Erythromycin Propionate, Erythromycin Stearate, Josamycin, Leucomycins, Midecamycins, Miokamycin, Oleandomycin, Primycin, Rokitamycin, Rosaramicin, Roxithromycin, Spiramycin, Troleandomycin), Polypeptides (Amphomycin, Bacitracin, Capreomycin, Colistin, Enduracidin, Enviomycin, Fusafungine, Gramicidin S, Gramicidin(s), Mikamycin, Polymyxin, Pristinamycin, Ristocetin, Teicoplanin, Thiostrepton, Tuberactinomycin, Tyrocidine, Tyrothricin, Vancomycin, Viomycin, Virginiamycin, Zinc Bacitracin), Tetracyclines(Apicycline, Chlortetracycline, Clomocycline, Demeclocycline, Doxycycline, Guamecycline, Lymecycline, Meclocycline, Methacycline, Minocycline, Oxytetracycline, Penimepicycline, Pipacycline, Rolitetracycline, Sancycline, Tetracycline), Cycloserine, Mupirocin, Tuberin; synthetic antibacterial agents, e.g. 2,4-Diaminopyrimidines (Brodimoprim, Textroxoprim, Trimethoprim), Nitrofurans (Furaltadone, Furazolium Chloride, Nifuradene, Nifuratel, Nifurfoline, Nifurpirinol, Nifurprazine, Niftirtoinol, Nitrofirantoin), Quinolones and Analogs (Cinoxacin, Ciprofloxacin, Clinafloxacin, Difloxacin, Enoxacin, Fleroxacin, Flumequine, Grepafloxacin, Lomefloxacin, Miloxacin, Nadifloxacin, Nalidixic Acid, Norflaxacin, Ofloxacin, Oxolinic Acid, Pazufloxacin, Pefloxacin, Pipemidic Acid, Piromidic Acid, Rosoxacin, Rufloxacin, Sparfloxacin, Temafloxacin, Tosufloxacin, Trovafloxacin), Sulfonamides (Acetyl Sulfamethoxypyrazine Benzylsulfamide, Chloramine-B, Chloramine-T, Dichioramine T, $N_2$-Formylsulfisomide, $N_4$-βD-Glucosylsulfanilamide, Mafenide, 4'-(Methylsulfamoyl)sulfanilanilide, Noprylsulfamide, Phthalylsulfacetamide, Phthalylsulfathiazole, Salazosulfadimidine, Succinylsulfathiazole, Sulfabenzamide, Sulfacetamide, Sulfachlorpyridazine, Sulfachrysoidine, Sulfacytine, Sulfadiazine, Sulfadicramide, Sulfadimethoxine, Sulfadoxine, Sulfaethidole, Sulfaguanidine, Sulfaguanol, Sulfalene, Sulfaloxic, Sulfamerazine, Sulfameter, Sulfamethazine, Sulfamethizole, Sulfamethomidine, Sulfamethoxazole, Sulfamethoxypyridazine, Sulfametrole, Sulfamidocbrysoidine, Sulfamoxole, Sulfanilamide, 4-Sulfanilamidosalicylic Acid, $N_4$-Sulfanilylsulfanilamide, Sulfanilylurea, N-Sulfanilyl-3,4-xylamide, Sulfanitran, Sulfaperine, Sulfaphenazole, Sulfaproxyline, Sulfapyrazine, Sulfapyridine, Sulfasomizole, Sulfasymazine, Sulfathiazole, Sulfathiourea, Sulfatolamide, Sulfisomidine, Sulfisoxazole), Sulfones (Acedapsone, Acediasulfone, Acetosulfone Sodium, Dapsone, Diathymosulfone, Glucosulfone Sodium, Solasulfone, Succisulfone, Sulfanilic Acid, p-Sulfanilylbenzylamine, Sulfoxone Sodium, Thiazolsulfone), Clofoctol, Hexedine, Methenamine, Methenamine Anhydromethylenecitrate, Methenamine Hippurate, Methenamine Mandelate, Methenamine Sulfosalicylate, Nitroxoline, Taurolidine, Xibomol; leprostatic antibacterial agents, such as Acedapsone, Acetosulfone Sodium, Clofazimine, Dapsone, Diathymosulfone, Glucosulfone Sodium, Hydnocarpic Acid, Solasulfone, Succisulfone, Sulfoxone Sodium, antifungal agents, such as Allylamines Butenafine, Naftifine, Terbinafine, Imidazoles (e.g., Bifonazole, Butoconazole,Chlordantoin, Chlormidazole, Cloconazole, Clotrimazole, Econazole, Enilconazole, Fenticonazole, Flutrimazole, Isoconazole, Ketoconazole, Lanoconazole, Miconazole, Omoconazole, Oxiconazole Nitrate, Sertaconazole, Sulconazole, Tioconazole), Thiocarbamates (Tolcilate, Tolindate, Tolnaftate), Triazoles (Fluconazole, Itraconazole, Saperconazole, Terconazole), Acrisorcin, Amorolfine, Biphenamine, Bromosalicylchloranilide, Buclosamide, Calcium Propionate, Chlorphenesin, Ciclopirox, Cloxyquin, Coparaffinate, Diamthazole Dihydrochloride, Exalamide, Flucytosine, Halethazole, Hexetidine, Loflucarban, Nifuratel, Potassium Iodide, Propionic Acid, Pyrithione, Salicylanilide, Sodium Propionate, Sulbentine, Tenonitrozole, Triacetin, Ujothion, Undecylenic Acid, Zinc Propionate; and the like.

Other antimicrobial agents useful in the present invention include β-lactamase inhibitors (e.g. Clavulanic Acid, Sulbactam, Tazobactam); Chloramphenicols (e.g. Azidamphenicol, Chioramphenicol, Thiamphenicol); Fusidic Acid; synthetic agents such as Trimethoprim, optionally in combination with sulfonamides) and Nitroimidazoles (e.g., Metronidazole, Tinidazole, Nimorazole); Antimycobacterial agents (e.g. Capreomycin, Clofazimine, Dapsone, Ethambutol, Isoniazid, Pyrazinamide, Rifabutin, Rifampicin, Streptomycin, Thioamides); Antiviral agents (e.g., Acyclovir Amantadine, Azidothymidine, Ganciclovir, Idoxuridine, Tribavirin, Trifluridine, Vidarabine); Interferons (e.g. Interferon α, Interferon β); and antiseptic agents (e.g., Chiorhexidine, Gentian violet, Octenidine, Povidone Iodine, Quaternary ammonium compounds, Silver sulfadiazine, Triclosan).

The antimicrobial agent can include agents that treat diseases caused by gram-positive and/or gram-negative bacteria. Preferred antimicrobial agents include, but are not limited to, amikacin, gentamicin, tobramycin, vancomycin, and salts thereof.

The therapeutic substance can further comprise a biological therapeutic substance, such as, e.g., a protein. Bone associated proteins can be added to modify the physical properties of the composition, enhance resorption, angiogenesis, cell entry and proliferation, mineralization, bone formation, growth of osteoclasts and/or osteoblasts, or the like. Proteins of particular interest are the different types of collagen, particularly Type I. Other proteins include osteonectin, bone sialoproteins (Bsp), alpha-2HS-glycoproteins, bone Gla-protein (Bgp), matrix Gla-protein, bone phosphoglycoprotein, bone phosphoprotein, bone proteoglycan, proteolipids, bone morphogenic proteins (e.g., BMP-1, -2A, -2B, -3, -3b, -4, -5, -6, -7, -8, -8b, -9, -10, -11, -12, -13, -14, -15), cartilage induction factor, platelet derived growth factor (PDGF-, -2), endothelial cell growth factors ((ECGF-1, -2a, -2b), skeletal growth factor (SKF=IGF-2). insulin-like growth factors (IGF-1, IGF-2), fibroblast growth factor (ODGF-1, -2, -3, -4, -5, -6, -7, -8, -9, -10, -11, -12, -13, -14, -15, -16, -17, -18, -19, -20, -21, -22, -23), colony stimulating factor, transforming growth factor ((e.g., TGF-fβ), vascular endothelial growth factors (VEGF), growth/differentiation factors (GDF-1, -3, -5, -6, -7, -8, -9, -9B, -10, -11, -15, -16), osteogenic proteins (OP-1=BMP -7, OP-2=BMP-8, OP-3=BMP-8b), brown growth hormone, parathyroid hormone (PTH), insulin, calcitonin, and the like. The proteins can also include proteins associated with cartilage, such as chondrocalcining protein; proteins associated with dentin, such as phosphophoryn, glycoproteins and Gla proteins; or proteins associated with enamel, such as amelogenin and enamelin. Structural proteins of interest include fibrin, fibrinogen, keratin, tubulin, elastin, and the like. Blood proteins can be employed, individually or together, in plasma or serum, e.g., serum albumin.

The therapeutic substance can further comprise a non-protein growth factor such as prostaglandins and statins (e.g, Simvastatin, Lovastatin).

In one embodiment, the therapeutic substance is a growth factor such as, but not limited to, bone morphogenetic proteins, endothelial cell growth factors, insulin-like growth factors, or the like, or a combination thereof.

Any suitable amount of therapeutic substance can be used. For example, the amount of antimicrobial agent that is present in the composition can be an amount sufficient to provide for a product that at least reduces the growth rate of microbial organisms in the region of the product as compared to a control. In many embodiments, the amount of antibiotic will be sufficient to provide for a zone of inhibition having a diameter of at least about 10 mm, usually at least about 15 mm, as measured by the antibiotic activity assay as described U.S. Pat. No. 5,968,253 to Poser et al., the entire content of which is expressly incorporated herein by reference. The amount of therapeutic substance used in the composition can vary depending on factors such as location of the repair, age and health of the patient, and the like, and can be determined by one skilled in the art.

Implant compositions comprising a therapeutic substance are also useful in the local delivery of such substance, e.g. to a physiological site of interest. For example, implant compositions comprising an antimicrobial agent are useful for methods requiring release of an antimicrobial agent into a local environment over an extended period of time, where the period of time is generally at least about 5, usually at least about 10, and more usually at least about 20 days, where the implant compositions may release the antimicrobial agent into their local environment for as long as 40 days or longer, depending on the specific composition from which the product is prepared. Thus, the compositions comprising an antimicrobial agent find use as extended antimicrobial agent delivery vehicles, i.e. as antimicrobial agent depots, in which the local delivery of an antimicrobial agent for an extended period of time is desired. The subject compositions find particular use as local antimicrobial agent delivery vehicles for bone tissue, particularly cancellous bone tissue.

In order to attain further improved mechanical properties (e.g., stiffness/modulus, toughness, compressive strength, shear strength, tensile strength, flexural strength, strain-to-break, fracture stress, ultimate tensile strength, tensile strength, tensile modulus, tensile toughness, or the like, or a combination thereof) for implantation or other particularly high-load or high-stress applications, the compositions according to the invention can optionally contain an array of organized fibers, e.g., constituting a mesh, continuous reinforcing fibers, or the like (hereinafter referred to generally as "continuous reinforcing fibers," for convenience only and without limiting what can be used as an array of organized fibers), to enhance the mechanical stability or to provide or enhance certain in situ mechanical characteristics of the composition. When used in the composition herein, the content and/or weight of the continuous reinforcing fibers should not used in determining concentration, percentages, or ratios of other components relative to the composition.

Suitable continuous reinforcing fibers according to the invention can be biodegradable, resorbable, and/or biocompatible and can include, but are not limited to, expandable and/or non-expandable meshes of metals, metal alloys, ceramics, polymers, copolymers, or the like, or a composite or mixture thereof; expandable and/or non-expandable bags or balloons containing metals, metal alloys, ceramics, polymers, copolymers, or the like, or a composite or mixture thereof; woven fabrics; knitted fabrics; cages of metals, metal alloys, ceramics, polymers, copolymers, or the like, or a composite or mixture thereof; molded porous forms made from metals, metal alloys, ceramics, polymers, copolymers, or the like, or a composite or mixture thereof; foams, e.g., polymeric, copolymeric, or composite; or the like; or a composite or combination thereof. Alternately, the continuous reinforcing fibers can be non-resorbable. Examples of continuous reinforcing fibers according to the invention can include, but are not limited to, braided nylon fiber (mesh), woven cotton fibers, knitted cotton fibers, cotton cheesecloth, polylactide (co)polymer cable mesh, braided and/or coated resorbable sutures, multifilament polymeric resorbable spool (made into a mesh), those resorbable and/or biocompatible molded meshes sold by Synthes Maxillofacial of Paoli, Pa., stainless steel screen, titanium cage, woven mesh bags such as those sold under the tradename OPTIMESH commercially available from Spinology (Minn.), or the like, or combinations thereof.

The addition of continuous reinforcing fibers with the composition according to the invention can advantageously cause increases in certain mechanical properties (e.g., flexural strength, screw pullout strength, flexural toughness, fracture toughness, flexural fatigue life, strain-to-break, fracture stress, ultimate tensile strength, tensile strength, tensile modulus, tensile toughness, and the like, and combinations thereof) of the composition, as compared to the same mechanical properties of the composition alone (or alternately of the calcium salt-containing component alone). In one embodiment, the presence of continuous reinforcing fibers in the composite results in a flexural strength increase of at least about 10%, preferably at least about 20%, more preferably at least about 50%, for example at least about 100%, at least about 200%, or at least about 350%. In this embodiment, the presence of continuous reinforcing fibers in the composite can generally result in a flexural strength increase of less than about 1000%, typically less than about 900%, for example not more than about 800% or not more than about 700%. In another embodiment, presence of continuous reinforcing fibers in the composite results in a screw pullout strength increase of at least about 50%, preferably at least about 75%, for example at least about 100%, at least about 125%, or at least about 150%. In this embodiment, the presence of continuous reinforcing fibers in the composite can generally result in a screw pullout strength increase of less than about 900%, typically less than about 800%, for example not more than about 700% or not more than about 600%. In still another embodiment, the presence of continuous reinforcing fibers in the composite results in an increase in the flexural toughness (as used herein, "flexural toughness" is defined as the area under the flexural load/stress vs. displacement/strain curve in a flexural strength test, e.g., a test done according to ASTM C1161 standard testing methods) of at least about 25-fold, preferably at least about 35-fold, for example at least about 50-fold, at least about 60-fold, at least about 75-fold, or at least about 100-fold.

In some embodiments, when continuous reinforcing fibers are added, it is preferable that the advantageous increases in certain mechanical properties by the introduction of the continuous reinforcing fibers is not accompanied by large decreases in other physical and/or mechanical properties (e.g., compressive strength, indentation strength, moldability/injectability, setting time, and the like, and combinations thereof) that can be crucial to the performance of the composition compositions according to the invention in their (in vivo) applications. In one embodiment, the presence of continuous reinforcing fibers in the composite can generally result in a compressive strength decrease of less than about 20%, typically less than about 10%, for example not more than about 8% or not more than about 5%.

In another embodiment, where the composition according to the invention is processed using conventional viscoelastic-liquid forming or liquid-setting means (e.g., by flow through an aperture such as injection or by unrestrained flow such as pouring, molding by hand, or the like, or a combination thereof), the continuous reinforcing fibers can be utilized for its capacity to direct compositional flow into, onto, within, and/or proximal to a bone void/defect. In this embodiment, when the continuous reinforcing fibers material is relatively uniformly expandable or non-expandable, the flow direction can be primarily through and/or away from the continuous reinforcing fibers material, or alternately, where the continuous reinforcing fibers is selectively relatively more expandable in one or more locations/regions and relatively less or non-expandable in others, the flow direction can advantageously (and secondarily) be away from the relatively less- or non-expandable locations/regions and thus toward the relatively more expandable locations/regions.

When one or more continuous reinforcing fibers are used in the composition according to the invention, the dimension(s) of the continuous reinforcing fibers will typically be determined relative to the dimension(s) of the void(s) and/or defect(s) being filled/treated. Alternately or additionally, other factors in determining the dimension(s) of the continuous reinforcing fibers can include, but are not limited to, the dimension(s) of the void(s) and/or defect(s), the amount of the composition being used to fill/treat the void(s) and/or defect(s), the location(s) of the void(s) and/or defect(s), the level of mechanical stability required by an implant in the void(s) and/or defect(s), or the like, or some combination thereof.

In order to have the capability to be formed into a unitary shape for implantation or other applications, the compositions according to the invention typically have liquid components (which include not only liquids but those viscous and/or particulate solids that are dissolved or are easily dissolvable in the liquids, e.g., setting solution, salt(s) contained therein, flow additive(s) if present, and the like) and solid components (which include those solid materials that are not dissolved or are not easily dissolvable in the liquids, e.g., calcium phosphate-containing compounds defined above, other relatively insoluble calcium salts, other relatively insoluble phosphate salts, fibers, and the like, but not including any continuous reinforcing fibers, if present). The ratio of these two types of components is termed the composite's liquid/solid, or L/S, ratio. Advantageously, the L/S ratio of the composition should be such that the composition is capable of being formed (e.g., by hand, by conventional solid mechanical forming means, by conventional viscoelastic/setting liquid forming means, or the like, or some hybrid variation thereof) into a feasible shape for the desired application and such that the composition is capable of holding substantially that shape until sufficient setting can occur. In one embodiment, the L/S ratio is greater than about 0.3, preferably greater than about 0.4, for example greater than about 0.41, greater than about 0.45, or greater than about 0.50. In another embodiment, the L/S ratio is less than about 0.8, preferably less than about 0.7, for example less than about 0.60. In a preferred embodiment, the L/S ratio can be from about 0.41 to about 0.55, alternately from about 0.47 to about 0.53, from about 0.42 to about 0.47, or from about 0.41 to about 0.45. In another preferred embodiment, the L/S ratio can be about 0.48, alternately about 0.42, about 0.45, or about 0.52. In another embodiment, the L/S ratio can be from greater than 0.50 to about 0.60 or from greater than 0.50 to about 0.55. In yet another embodiment, the L/S ratio can be from greater than 0.45 to less than 0.50 or from about 0.46 to less than 0.50. In a preferred embodiment, the L/S ratio is about 0.50.

Another aspect of the invention relates to a process for making and implanting a composition comprising a calcium salt-containing component (e.g., a bone cement), a plurality of discrete fibers, optionally a flow additive, and optionally continuous reinforcing fibers or fiber mesh, which composition can advantageously be at least partially biodegradable, at least partially resorbable, and/or at least partially biocompatible. This process can have the following steps, although it should be appreciated that the following order can be varied:

- optionally grind the calcium salt-containing component, especially when relatively small particle sizes of this component are desirable;
- optionally incorporate a flow additive described above, particularly for compositions processed using conventional viscoelastic-liquid forming or liquid-setting means (e.g., by flow through an aperture such as injection or by unrestrained flow such as pouring, molding by hand, or the like, or a combination thereof);
- optionally, incorporate demineralized bone (e.g., by hand, using a rotary mixer, or using a pneumatic mixer) to form a calcium salt/demineralized bone-containing component;
- incorporate a plurality of discrete fibers (e.g., by hand, using a rotary mixer, or using a pneumatic mixer) to form a fiber-reinforced, calcium salt-containing component;
- optionally treat a void and/or defect (e.g., in a bone), and/or an in vivo area proximal thereto, for receiving the composition according to the invention;
- optionally position and/or anchor continuous reinforcing fibers near, around, and/or within the void and/or defect, particularly for compositions processed using conventional viscoelastic-liquid forming or liquid-setting means (e.g., by flow through an aperture such as injection or by unrestrained flow such as pouring, molding by hand, or the like, or a combination thereof);
- introduce the fiber-reinforced, component into, onto, and/ or proximal to the void and/or defect in order to at least partially coat and/or fill the void and/or defect, thus forming an implantable fiber-reinforced composite material; and
- optionally treat the at least partially coated and/or filled void and/or defect containing the implantable fiber-reinforced composite material and/or the in vivo area proximal thereto to form a biocompatible and/or semi-permeable surface (e.g., by exposing the available surface to a catalytic and/or reactive compound to chemically alter the available surface; to set or to hasten the setting of the composition at the available surface; to protect the available surface, and optionally the entire implantable fiber-reinforced composite material, from undesired immune response; to induce at the available surface, and/or optionally within the entire implantable fiber-reinforced composite material, an increased immune response; to establish a semi-permeable layer through which and/or into which only certain desirable biological compounds may pass, while excluding certain other undesirable biological compounds; or the like; or some combination thereof).

In an alternate embodiment, the process according to the invention can have the following steps, although it should be appreciated that the following order can be varied:

- optionally grind the calcium salt-containing component, especially when relatively small particle sizes of this component are desirable;
- incorporate a flow additive described above to form a flowable composition, optionally with demineralized bone, particularly for compositions processed using conventional viscoelastic-liquid forming or liquid-setting means (e.g., by flow through an aperture such as injection or by unrestrained flow such as pouring, molding by hand, or the like, or a combination thereof);
- optionally, incorporate demineralized bone (e.g., by hand, using a rotary mixer, or using a pneumatic mixer) to form a calcium salt/demineralized bone-containing component;
- optionally incorporate a plurality of discrete fibers (e.g., by hand, using a rotary mixer, or using a pneumatic mixer) described above;
- optionally treat a void and/or defect (e.g., in a bone), and/or an in vivo area proximal thereto, for receiving the composition according to the invention;
- optionally position and/or anchor continuous reinforcing fibers near, around, and/or within the void and/or defect, particularly for compositions processed using conventional viscoelastic-liquid forming or liquid-setting means (e.g., by flow through an aperture such as injection or by unrestrained flow such as pouring, molding by hand, or the like, or a combination thereof);
- introduce the flowable component into, onto, and/or proximal to the void and/or defect in order to at least partially coat and/or fill the void and/or defect, thus forming an implantable composite material; and
- optionally treat the at least partially coated and/or filled void and/or defect containing the implantable composite material and/or the in vivo area proximal thereto to form a biocompatible and/or semi-permeable surface (e.g., by exposing the available surface to a catalytic and/or reactive compound to chemically alter the available surface; to set or to hasten the setting of the composition at the available surface; to protect the available surface, and optionally the entire implantable composite material, from undesired immune response; to induce at the available surface, and/or optionally within the entire implantable composite material, an increased immune response; to establish a semi-permeable layer through which and/ or into which only certain desirable biological compounds may pass, while excluding certain other undesirable biological compounds; or the like; or some combination thereof).

Another aspect of the invention relates to a method for treating a bone defect or for filling a bone void by providing an implantable composition according to the invention, which can advantageously be at least partially biodegradable, at least partially resorbable, and/or at least partially biocompatible. This process can have the following steps, although it should be appreciated that the following order can be varied:

optionally grind the calcium salt-containing component, especially when relatively small particle sizes of this component are desirable;

optionally incorporate the flow additive described above, optionally with demineralized bone, particularly for compositions processed using conventional viscoelastic-liquid forming or liquid-setting means (e.g., by flow through an aperture such as injection or by unrestrained flow such as pouring, molding by hand, or the like, or a combination thereof);

optionally, incorporate demineralized bone (e.g., by hand, using a rotary mixer, or using a pneumatic mixer) to form a calcium salt/demineralized bone-containing component;

incorporate a plurality of discrete fibers (e.g., by hand, using a rotary mixer, or using a pneumatic mixer) to form a fiber-reinforced, calcium salt-containing component;

optionally pre-treat a void and/or defect (e.g., in a bone), and/or an in vivo area proximal thereto, for receiving the composition according to the invention;

optionally position and/or anchor continuous reinforcing fibers near, around, and/or within the void and/or defect, particularly for compositions processed using conventional viscoelastic-liquid forming or liquid-setting means (e.g., by flow through an aperture such as injection or by unrestrained flow such as pouring, molding by hand, or the like, or a combination thereof);

introduce the fiber-reinforced, calcium salt-containing component into, onto, and/or proximal to the void and/or defect in order to at least partially coat and/or fill the void and/or defect, thus forming an implantable fiber-reinforced composite material; and optionally post-treat the at least partially coated and/or filled void and/or defect containing the implantable fiber-reinforced composite material and/or the in vivo area proximal thereto to form a biocompatible and/or semi-permeable surface (e.g., by exposing the available surface to a catalytic and/or reactive compound to chemically alter the available surface; to set or to hasten the setting of the composition at the available surface; to protect the available surface, and optionally the entire implantable fiber-reinforced composite material, from undesired immune response; to induce at the available surface, and/or optionally within the entire implantable fiber-reinforced composite material, an increased immune response; to establish a semi-permeable layer through which and/or into which only certain desirable biological compounds may pass, while excluding certain other undesirable biological compounds; or the like; or some combination thereof).

In an alternate embodiment, the method for treating a bone defect or for filling a bone void according to the invention can have the following steps, although it should be appreciated that the following order can be varied:

optionally grind the calcium salt-containing component, especially when relatively small particle sizes of this component are desirable;

incorporate a flow additive described above to form a flowable calcium phosphate-containing composition, particularly for compositions processed using conventional viscoelastic-liquid forming or liquid-setting means (e.g., by flow through an aperture such as injection or by unrestrained flow such as pouring, molding by hand, or the like, or a combination thereof);

optionally, incorporate demineralized bone (e.g., by hand, using a rotary mixer, or using a pneumatic mixer) to form a calcium salt/demineralized bone-containing component;

optionally incorporate a plurality of discrete fibers (e.g., by hand, using a rotary mixer, or using a pneumatic mixer) described above;

optionally pre-treat a void and/or defect (e.g., in a bone), and/or an in vivo area proximal thereto, for receiving the composition according to the invention;

optionally position and/or anchor continuous reinforcing fibers near, around, and/or within the void and/or defect, particularly for compositions processed using conventional viscoelastic-liquid forming or liquid-setting means (e.g., by flow through an aperture such as injection or by unrestrained flow such as pouring, molding by hand, or the like, or a combination thereof);

introduce the flowable calcium salt-containing component into, onto, and/or proximal to the void and/or defect in order to at least partially coat and/or fill the void and/or defect, thus forming an implantable composite material; and optionally post-treat the at least partially coated and/or filled void and/or defect containing the implantable composite material and/or the in vivo area proximal thereto to form a biocompatible and/or semi-permeable surface (e.g., by exposing the available surface to a catalytic and/or reactive compound to chemically alter the available surface; to set or to hasten the setting of the composition at the available surface; to protect the available surface, and optionally the entire implantable composite material, from undesired immune response; to induce at the available surface, and/or optionally within the entire implantable composite material, an increased immune response; to establish a semi-permeable layer through which and/or into which only certain desirable biological compounds may pass, while excluding certain other undesirable biological compounds; or the like; or some combination thereof).

Another aspect of the present invention relates to a kit or packaging system for storing, preparing, mixing, and/or administering compositions according to the invention. Advantageously, the kit or packaging system can contain the composite components in at least two separate compartments. In this embodiment, the solid portion of the calcium salt-containing component according to the invention (e.g., bone cement) can be present in one compartment, which can optionally also contain the fiber component(s) to form a solid or "dry" components compartment, while the liquid portion of the calcium salt-containing component according to the invention (e.g., setting solution) can be present in another compartment, which can optionally also contain the flow additive component to form a liquid or "wet" components compartment. A non-limiting example of a two-compartment kit is described in U.S. Pat. No. 6,149,655, the entire content of which is hereby incorporated by express reference hereto.

The composition of the present invention can optionally comprise one or more detergent or surfactants to improve the mixing properties and consistency of the cements. When used, the detergent or surfactant is present in an amount from about 0.01% by weight to about 2.5% by weight based on the total weight of the liquid and dry components of the composition.

Non-limiting examples of useful surfactants and detergents include anionic surfactants such as, e.g., docusate sodium, sodium dodecyl sulphate and sodium lauryl sulfate; non-ionic surfactants such as, e.g., stearic acid, cetrimide, glycerin monooleate, polyoxyethylene (20) sorbitan monooleate, polyoxyethylene (4) sorbitan monolaurate, polyoxyethylene (20) sorbitan monopalmitate, polyoxyethylene (20) sorbitan monostearate, polyoxyethylene (4) sorbitan monostearate, polyoxyethylene (20) sorbitan tristearate, polyoxyethylene (20) sorbitan monooleate, polyoxyethylene (5) sorbitan monooleate, polyoxyethylene (20) sorbitan trioleate, polyoxyethylene (20) sorbitan monoisostearate, polyvinyl alcohol, sorbitan di-isostearate, sorbitan dioleate, sorbitan monoisostearate, sorbitan monolaurate, sorbitan monooleate, sorbitan monopalmitate, sorbitan monostearate, sorbitan sesqui-isostearate, sorbitan sesquioleate, sorbitan sesquistearate, sorbitan triisostearate, sorbitan trioleate, sorbitan tristearate, glyceryl monooleate, isopropyl myristate, isopropyl palpitate, lanolin, lanolin alcohols, hydrous lanolin, lecithin, triglycerides, monoethanolamine, oleic acid, polyethylene glycol, polyethylene glycol monocetyl ether, polyethylene glycol monostearyl ether, polyethylene glycol monolauryl ether, polyethylene glycol monooleyl ether, polyethoxylated castor oil, polypropylene glycol, polyoxyl 40 stearate, polyoxyl 50 stearate, triethanolamine, methyl cellulose, carboxymethyl cellulose, hydroxypropylmethyl cellulose, and copolymers of ethylene oxide and propylene oxide such as PLURONIC® surfactants (available from BASF, Mount Olive, N.J.); and cationic surfactants such as, e.g., alkyldimethyl(phenylmethyl)ammonium chloride and benzethonium chloride; and combinations thereof.

After mixing, the cement of the invention is applied to the bone void and/or bone defect and allowed to stand for a time and at a temperature sufficient to form a hardened cement. The time required for the cement to harden will vary depending, for example, on the composition of the cement such as water content, pH, presence of additives, amount and type of fiber, and temperature. Typically, a time sufficient for the cement to harden is from about 5 minutes to about 60 minutes, preferably from about 5 minutes to about 20 minutes. A temperature sufficient for the cement to harden is typically from about 0° C. to about 45° C., more preferably from about 20° C. to about 40° C., most preferably about normal physiological temperature, i.e., 37° C.

If desired, the hardening time can be accelerated (shortened) by adding an accelerator. For example, the hardening time of the cement can be accelerated by using a liquid component having a high concentration of an additional water-soluble salt such as sodium succinate, sodium lactate, sodium acetate and sodium chloride (see U.S. Pat. No. 5,152,836 to Hirano et al.). For example, when the liquid component contains an additional salt to accelerate the hardening time of the cement, the additional salt is present in an amount not more than about 30 wt % based on the weight of the liquid component.

Additionally or alternately, a kit or system according to the invention can include aspects of those kits and/or systems described in U.S. Pat. Nos. 6,083,229 and 6,149,655, the entire content of which is hereby incorporated by express reference hereto.

The percent retention of the aforementioned mechanical properties or the aforementioned molecular weights is expressed herein either as a proportion based on the properties of the pre-mixed, unused fibers, or based on the properties of the composition without any fibers added (e.g., the pure implantable calcium salt-containing component or bone cement), as applicable.

EXAMPLES

Preferred embodiments of the present invention and comparative embodiments will be illustrated by reference to the following examples, which are included to exemplify, but in no way limit, the scope of the present invention.

Comparative Example 1

Prior Art Bone Cement Compositions

The specific bone cement compositions used for comparison herein are listed in Table 1 below.

TABLE 1

| Compar. Ex. # | $Ca(H_2PO_4)_2 \cdot H_2O$ | $\alpha\text{-}Ca_3(PO_4)_2$ | $CaCO_3$ | $BaSO_4$ | $Na_2HPO_4$ sol'n |
|---|---|---|---|---|---|
| 1A | 3.3 | 84.4 | 12.4 | — | 0.075 m, L/S = 0.48 |
| 1B | 2.9 | 73.4 | 10.7 | 13 | 0.075 m, L/S = 0.45 |
| 1C | 3.3 | 84.4 | 12.4 | — | 0.075 m, L/S = 0.52 |

Comparative Example 1A is adapted from a cement commercially available from Norian Corp. of Chester, Pa. under the tradename NORIAN SRS®. Comparative Example 1B is a radiopaque cement commercially available from Norian Corp. of West Chester, Pa. under the tradename NORIAN XR™. Comparative Example 1C is adapted from a fast set cement commercially available from Norian Corp. of Chester, Pa. under the tradename NORIAN CRS®, by changing the $Na_2HPO_4$ content from about 0.15 m to about 0.075 m and by changing the L/S ratio from about 0.56 to about 0.52.

Example 1

Implantable Compositions According to the Invention Containing Resorbable Fibers Specific fiber-reinforced compositions are listed in Table 2 below.

TABLE 2

| Example # | Calcium Phosphate Composition | Resorbable Fibers |
|---|---|---|
| 1D | Comparative Example 1A | 1% (3 mm × 16-20 μm) L6 fibers |
| 1E | Comparative Example 1A | 2% (3 mm × 16-20 μm) L6 fibers |
| 1F | Comparative Example 1A | 2% (6 mm × 16-20 μm) L6 fibers |
| 1G | Comparative Example 1A | 1% (8 mm × 16-20 μm) L6 fibers |
| 1H | Comparative Example 1A | 2% (8 mm × 16-20 μm) L6 fibers |
| 1J | Comparative Example 1A | 2% (8 mm × 16-20 μm) L6 dogbone fibers |

TABLE 2-continued

| Example # | Calcium Phosphate Composition | Resorbable Fibers |
|---|---|---|
| 1K | Comparative Example 1A | 1% (3 mm × 16-20 μm) LACTOMER fibers |
| 1L | Comparative Example 1A | 2% (3 mm × 16-20 μm) LACTOMER fibers |
| 1M | Comparative Example 1A | 2% (3 mm long) LACTOMER 9-1 fibers |

L6 fibers are chopped copolymer fibers of 82% glycolide and 18% lactide (wt:wt) and are commercially available from U.S. Surgical of New Haven, CT. L6 dogbone fibers have the fiber ends altered so that the fibers are in the shape of a dogbone or dumbbell. LACTOMER fibers are glycolide-L-lactide copolymer fibers commercially available from U.S. Surgical of New Haven, Conn. LACTOMER 9-1 fibers are chopped multifilament (i.e., ≧5-fiber) spools.

The compositions of Examples 1D-1M above were formed by mixing the solid components of the bone cement of Comparative Example 1A with the respective amount and type of resorbable fibers, grinding the mixture in a mortar-and-pestle, adding the liquid components of the bone cement of Comparative Example 1A, forming the resulting slurry into a standard shape (for subsequent testing), and allowing that shaped slurry to set for at least 24 hours.

Example 2

Implantable Compositions According to the Invention Containing Continuous Reinforcing Fibers Specific continuous fiber- or fiber mesh-reinforced compositions are listed in Table 3 below.

TABLE 3

| Example # | Calcium Phosphate Composition | Continuous fiber or Fiber Mesh |
|---|---|---|
| 2A | Comparative Example 1A | LACTOMER Cable Mesh |
| 2B | Comparative Example 1A | Cotton Cheesecloth |

LACTOMER cable mesh contains twisted and braided glycolide-L-lactide copolymer fibers and is commercially available from U.S. Surgical of New Haven, CT.

The compositions of Examples 2A-2B above were formed by grinding the solid components of the bone cement of Comparative Example 1A in a mortar-and-pestle, adding the liquid components of the bone cement of Comparative Example 1A, forming the resulting slurry into a standard shape (for subsequent testing), positioning the continuous reinforcing fibers or fiber mesh around the outside of the shaped slurry, applying gentle pressure to imbed the continuous reinforcing fibers or fiber mesh therein, and allowing that continuous fiber-reinforced form to set for at least 24 hours.

Example 3

Implantable Compositions According to the Invention Containing a Flow Additive

Specific flowable/injectable compositions are listed in Table 4 below.

TABLE 4

| Example # | Calcium Phosphate Composition | Flow Additive[1] | $Na_2HPO_4$ sol'n |
|---|---|---|---|
| 3A | Comparative Example 1A | 0.3 wt % Sodium Hyaluronate | 0.15 m, L/S = 0.48 |
| 3B | Comparative Example 1B | 0.3 wt % Sodium Hyaluronate | 0.075 m, L/S = 0.42 |
| 3C | Comparative Example 1B | 0.6 wt % Sodium Hyaluronate | 0.075 m, L/S = 0.42 |
| 3D | Comparative Example 1B | 0.6 wt % Sodium Hyaluronate | 0.075 m, L/S = 0.52 |
| 3E | Comparative Example 1B | 1.4 wt % Sodium Hyaluronate | 0.075 m, L/S = 0.42 |

[1]Based on the weight exclusive of the $Na_2HPO_4$ solution.

The flowable/injectable compositions of Examples 3A-3E above were formed by grinding the solid components of the bone cements of Comparative Example 1A or 1B in a mortar-and-pestle, adding the sodium hyaluronate-sodium phosphate solution and the liquid components of the bone cements of Comparative Example 1A or 1B, injecting that flowable/injectable composition into a standard shape (for subsequent testing), and allowing that shaped form to set for at least 24 hours.

Example 4

Implantable Compositions According to the Invention Containing Resorbable Fibers and a Flow Additive One specific flowable/injectable fiber-reinforced composition is listed in Table 5 below.

TABLE 5

| Example # | Calcium Phosphate Composition | Flow Additive[1] | Resorbable Fibers[2] |
|---|---|---|---|
| 4A | Comparative Example 1A | 03 wt % Sodium Hyaluronate | 1% (3 mm × 16-20 μm) LACTOMER fibers |

[1]Based on the weight exclusive of the $Na_2HPO_4$ solution.
[2]LACTOMER fibers are glycolide-L-lactide copolymer fibers commercially available from the U.S. Surgical of New Haven, CT.

The flowable/injectable fiber-reinforced composition of Example 4A above was formed by mixing the solid components of the bone cement of Comparative Example 1A with the resorbable fibers, grinding the mixture in a mortar-and-pestle, adding the flow additive and the liquid components of the bone cement of Comparative Example 1A, injecting that flowable/injectable fiber-reinforced composition into a standard shape (for subsequent testing), and allowing that shaped slurry to set for at least 24 hours.

Example 5

Implantable Compositions According to the Invention Containing Resorbable Fibers and Continuous Reinforcing Fibers One specific fiber-reinforced and mesh-reinforced composition is listed in Table 6 below.

TABLE 6

| Example # | Calcium Phosphate Comp. | Non-Resorbable Fibers[1] | Stent or Fiber Mesh |
|---|---|---|---|
| 5A | Comparative Example 1A | 1% (3 mm × 16-20 μm) Lactomer fibers | Lactomer Cable Mesh |

[1]LACTOMER fibers are glycolide-L-lactide copolymer fibers commercially available from U.S. Surgical of New Haven, CT. LACTOMER cable mesh contains twisted and braided glycolide-L-lactide copolymer fibers.

The composition of Example 5A above was formed by mixing the solid components of the bone cement of Comparative Example 1A with the respective amount and type of resorbable fibers, grinding the mixture in a mortar-and-pestle, adding the liquid components of the bone cement of Comparative Example 1A, forming the resulting slurry into a standard shape (for subsequent testing), positioning the continuous reinforcing fibers or fiber mesh around the outside of the shaped slurry, applying gentle pressure to imbed the continuous reinforcing fibers or fiber mesh therein, and allowing that continuous fiber-reinforced form to set for at least 24 hours.

Example 6

Implantable Compositions According to the Invention Containing Non-Resorbable Fibers One specific fiber-reinforced and mesh-reinforced composition is listed in Table 7 below.

TABLE 7

| Example # | Calcium Phosphate Comp. | Resorbable Fibers[1] |
|---|---|---|
| 6A | Comparative Example 1A | 2% (6-10 mm × 20 μm) fiberglass fibers |

[1]Fiberglass fibers are chopped E-glass fibers commercially available from Owens-Corning of Ohio.

The composition of Example 6A above was formed by mixing the solid components of the bone cement of Comparative Example 1A with the non-resorbable fibers, grinding the mixture in a mortar-and-pestle, adding the liquid components of the bone cement of Comparative Example 1A, forming the resulting slurry into a standard shape (for subsequent testing), and allowing that shaped slurry to set for at least 24 hours.

Example 7

Comparison of Flexural Strengths of Implantable Compositions According to the Invention The flexural strength of the compositions of Examples 1D-1J, 2A-2B, 5A, and 6A were compared to that of Comparative Example 1A (as a control). The results are shown in Table 8 below.

TABLE 8

| Example # | Reinforcing Components | Flexural Strength (ASTM C-1161) |
|---|---|---|
| 1A | None | ~5 MPa |
| 1D | 1% (3 mm × 16-20 μm) L6 fibers | 5.9 MPa |
| 1E | 2% (3 mm × 16-20 μm) L6 fibers | 10 MPa |
| 1F | 2% (6 mm × 16-20 μm) L6 fibers | 12.4 MPa |
| 1G | 1% (8 mm × 16-20 μm) L6 fibers | 6.9 MPa |
| 1H | 2% (8 mm × 16-20 μm) L6 fibers | 9.4 MPa |
| 1J | 2% (8 mm × 16-20 μm) L6 dogbone fibers | 8.8 MPa |
| 2A | LACTOMER Cable Mesh | 14.4 MPa |
| 2B | Cotton Cheesecloth | 8.4 MPa |
| 5A | 1% (3 mm × 16-20 μm) LACTOMER fibers AND LACTOMER Cable Mesh | 15.8 MPa |
| 6A | 2% (6-10 mm × 20 μm) fiberglass fibers | 8.9 MPa |

The compositions of Examples 1D-1J, 2A-2B, 5A, and 6A all showed improved flexural strength values with their reinforcing agents, with the best improvement (about a 216% increase) over the base bone cement of Comparative Example 1A being shown for the combination of resorbable fibers and a resorbable mesh "stent."

Example 8

Comparison of Screw Pullout Strengths of Implantable Compositions According to the Invention The screw pullout strength of the compositions of Examples 1K, 2A, and 5A were compared to that of Comparative Example 1A (as a control). The results are shown in Table 9 below.

TABLE 9

| Example # | Reinforcing Components[1,2] | Screw Pullout Strength |
|---|---|---|
| 1A | None | ~9.9 lbs-force |
| 1K | 1% (3 mm × 16-20 μm) LACTOMER fibers | 27.1 lbs-force |
| 2A | LACTOMER Cable Mesh | 33.6 lbs-force |
| 5A | 1% (3 mm × 16-20 μm) LACTOMER fibers AND LACTOMER Cable Mesh | 61 lbs-force |

[1]Based on the weight exclusive of the $Na_2HPO4$ solution.
[2]LACTOMER fibers are glycolide-L-lactide copolymer fibers commercially available from the U.S. Surgical of New Haven, CT.

The compositions of Examples 1K, 2A, and 5A all showed significant improvement in screw pullout strength values with their reinforcing agents, with the best improvement (about a 516% increase) over the base bone cement of Comparative Example 1A being shown for the combination of resorbable fibers and a resorbable mesh "stent."

Example 9

Comparison of Flexural Toughness of Implantable Compositions According to the Invention The flexural toughness of the compositions of Example 5A, as gleaned from the area under the load vs. extension flexural strength curves done according to ASTM C-1161 (curves not shown), was compared to that of Comparative Example 1A (as a control). The results are shown in Table 10 below.

TABLE 10

| Example # | Reinforcing Components[1,2] | Flexural Toughness (curve area/Ex. 1A curve area) |
|---|---|---|
| 1A | None | 1.0 |
| 5A | 1% (3 mm × 16-20 µm) LACTOMER fibers AND LACTOMER Cable Mesh | ~88 |

[1] Based on the weight exclusive of the $Na_2HPO_4$ solution.
[2] LACTOMER fibers are glycolide-L-lactide copolymer fibers commercially available from the U.S. Surgical of New Haven, CT.

The composition of Example 5A showed a significant improvement in flexural toughness values with their reinforcing agents, with about an 88-fold increase over the base bone cement of Comparative Example 1A being shown for the combination of resorbable fibers and a resorbable continuous reinforcing fiber mesh.

Example 10

Comparison of Compression Strengths of Implantable Compositions According to the Invention The compression strength of the compositions of Examples 1K, 3A, and 4A were compared to that of Comparative Example 1A (as a control). The results are shown in Table 11 below.

TABLE 11

| Example # | Non-Cement Components[1,2] | Compression Strength |
|---|---|---|
| 1A | None (L/S = 0.48) | 53.4 MPa |
| 1K | 1% (3 mm × 16-20 µm) LACTOMER fibers (L/S = 0.48) | 51 MPa |
| 3A | 0.3 wt % Sodium Hyaluronate (L/S = 0.48) | 46.1 MPa |
| 4A | 1% (3 mm × 16-20 µm) LACTOMER fibers AND 0.3 wt % Sodium Hyaluronate (L/S = 0.48) | 48.1 MPa |

[1] Based on the weight exclusive of the $Na_2HPO_4$ solution.
[2] LACTOMER fibers are glycolide-L-lactide copolymer fibers commercially available from the U.S. Surgical of New Haven, CT.

The compositions of Examples 1K, 3A, and 4A all showed relatively low deterioration of compression strength values with their relatively low amount of additional components. While the presence of the flow agent alone reduced the compressive strength of the composite a significant amount for only 0.3 wt % (about a 14% decrease from Comparative Example 1A), and while the presence of the resorbable fibers alone reduced the compressive strength of the composite a much smaller amount at a 1 wt % loading (only about a 4.5% decrease from Comparative Example 1A), the fiber-flow additive combination seemed to provide an intermediate compression strength loss (only about a 9.9% loss from Comparative Example 1A), despite a higher total component loading of 1.3 wt %. A synergistic combination of the fibers and the flow additive in Example 4A is thus indicated.

Example 11

Preparation of Compositions Containing Demineralized Bone and Calcium-Containing Cement Hyaluronic acid (0.30 parts by weight) was added to a ceramic mortar containing 55 parts by weight of 0.075 m $Na_2HPO_4$. To the resultant aqueous solution was added 7 parts by weight of demineralized bone powder (Musculoskeletal Transplant Foundation, Edison, N.J.), the resultant mixture stood for 3 minutes at 25°, and 93 parts by weight of NORIAN SRS (a commercial calcium bone cement available from Norian Corp., Paoli, Pa.) was added. The resultant mixture was ground with a pestle for 2 minutes at 25° C. to provide a demineralized bone/calcium calcium cement composite.

Example 12

Preparation of Fiber-Reinforced Compositions Containing Demineralized Bone and Calcium-Containing Cement The following method can be used to prepare a fiber-reinforced compositions containing demineralized bone and a calcium salt.

NORIAN SRS (93 parts by weight) and 1% (3 mm×16-20 µm) LACTOMER fiber (glycolide-L-lactide copolymer fiber available from U.S. Surgical, New Haven, Conn.) are ground together in a mortar and pestle to form a calcium salt/fiber paste and the mixture is dried to form a calcium salt/fiber mixture. In a separate mortar, hyaluronic acid (0.30 parts by weight) is added to a ceramic mortar containing 55 parts by weight of 0.075 m $Na_2HPO_4$. To the resultant aqueous solution is added 7 parts by weight of demineralized bone powder (Musculoskeletal Transplant Foundation, Edison, N.J.), the resultant mixture is allowed to stand for 3 minutes at 25° C., and the calcium salt/fiber mixture is added. The resultant mixture is ground with a pestle for 2 minutes at 25° C. to provide a fiber-reinforced demineralized bone/calcium calcium cement composite.

Example 13

Preparation of Fiber-Reinforced Calcium-Containing Cement

NORIAN SRS (97 parts by weight) and 3 parts by weight of LACTOMER fiber (glycolide-L-lactide, 82:18 (wt:wt) copolymer fiber available from U.S. Surgical, New Haven, Conn.) (1 mm×16 µm) were ground together in a mortar and pestle to form a calcium salt/fiber paste, and the mixture was dried to form a calcium salt/fiber mixture. Separately, sodium hyaluronate acid (0.25 parts by weight) was added to a ceramic mortar containing a solution of $Na_2HPO_4.7H_2O$ (0.58 parts by weight) and $NaH_2PO_4.H_2O$ (0.20 parts by weight) in water (48.9 parts by weight). The resultant mixture was allowed to stand for 3 minutes at 25° C., and the calcium salt/fiber mixture was added. The resultant mixture was ground with a pestle for 2 minutes at 25° C. to provide a fiber-reinforced calcium cement composite having a liquid to solid ratio of 0.5 and a viscosity of 50 cPs. The results of mechanical testing of the cement of Example 13 are shown in Table 12 below.

TABLE 12

| Test | Result |
|---|---|
| Flexural strength | 8 MPa |
| Flexural Modulus | 5-7 GPa |
| Flexural Work of Fracture | 900-1200 J/m$^2$ |
| Compressive Strength | 35-40 MPa |
| Compressive Modulus | 2-3 GPa |

Although the present invention is described with reference to certain preferred embodiments, it is apparent that modification and variations thereof can be made by those skilled in the art without departing from the scope or this invention, particularly as defined by the appended claims.

What is claimed is:

1. An implantable composition comprising:
   Solid components comprising (a) a calcium salt-containing component, wherein the calcium salt-containing component comprises one or more of amorphous calcium phosphate, crystalline calcium phosphate, $CaHPO_4$, $CaHPO_4 \cdot H_2O$, $\alpha$-$Ca_3(PO_4)_2$, $\alpha$-bar-$Ca_3(PO_4)_2$, $\beta$-$Ca_3(PO_4)_2$, $\gamma$-$Ca_3(PO_4)_2$, $Ca_5(PO_4)_3OH$, $Ca_4O(PO_4)_2$, $CaP_4O_{11}$, $\alpha$-$Ca_2P_2O_7$, $\beta$-$Ca_2P_2O_7$, $\gamma$-$Ca_2P_2O_7$, $Ca(H_2PO_4)_2 \cdot nH_2O$, where n is a real number from 0 to 5, $Ca_8H_2(PO_4)_6 \cdot 5H_2O$, $Ca(SO_4)_2$, $\alpha$-$Ca(SO_4)_2 \cdot 1/2H_2O$, or $\beta$-$Ca(SO_4)_2 \cdot 1/2H_2O$; or any combination thereof;
   (b) from about 1% to about 5% by weight of fibers comprising resorbable homopolymers or copolymers, the fibers having a fiber length of not more than about 15 mm, wherein a fiber surface is modified; and
   one or more liquid components.

2. The implantable composition of claim 1, further comprising demineralized bone.

3. The implantable composition of claim 1, wherein the ratio of liquid components to solid components is from 0.41 to 0.55.

4. The implantable composition of claim 1, exhibiting increase in flexure strength over compositions without discrete fibers from 50% to about 900%.

5. The implantable composition of claim 1, exhibiting increase over composition without discrete fibers in screw pullout strength from 75% to about 800%.

6. The implantable composition of claim 1, exhibiting increase over composition without discrete fibers in flexural toughness of at least 35- fold.

7. An implantable composition comprising:
   (a) a calcium salt-containing component, wherein the calcium salt-containing component comprises one or more of amorphous calcium phosphate, crystalline calcium phosphate, $CaHPO_4$, $CaHPO_4 \cdot H_2O$, $\alpha$-$Ca_3(PO_4)_2$, $\alpha$-bar-$Ca_3(PO_4)_2$, $\beta$-$Ca_3(PO_4)_2$, $\gamma$-$Ca_3(PO_4)_2$, $Ca_5(PO_4)_3OH$, $Ca_4O(PO_4)_2$, $CaP_4O_{11}$, $\alpha$-$Ca_2P_2O_7$, $\beta$-$Ca_2P_2O_7$, $\gamma$-$Ca_2P_2O_7$, $Ca(H_2PO_4)_2 \cdot nH_2O$, where n is a real number from 0 to 5, $Ca_8H_2(PO_4)_6 \cdot 5H_2O$, $Ca(SO_4)_2$, $\alpha$-$Ca(SO_4)_2 \cdot 1/2H_2O$, or $\beta$-$Ca(SO_4)_2 \cdot 1/2H_2O$; or any combination thereof;
   (b) a plurality of fibers comprising resorbable homopolymers or copolymers;
   (c) fibers comprising an array or mesh of resorbable homopolymer or copolymer fibers; and
   (d) demineralized bone.

8. The implantable composition of claim 1, exhibiting increase in flexural strength over composition without fibers in flexural strength from 50% to about 900%.

9. The implantable composition of claim 7, exhibiting increase over composition without discrete fibers in screw pullout strength from 75% to about 800%.

10. The implantable composition of claim 7, exhibiting increase over composition without fibers in flexural toughness of at least 35- fold.

11. An implantable composition comprising:
    (a) a calcium salt-containing component, wherein the calcium salt-containing component comprises one or more of amorphous calcium phosphate, crystalline calcium phosphate, $CaHPO_4$, $CaHPO_4 \cdot H_2O$, $\alpha$-$Ca_3(PO_4)_2$, $\alpha$-bar-$Ca_3(PO_4)_2$, $\beta$-$Ca_3(PO_4)_2$, $\gamma$-$Ca_3(PO_4)_2$, $Ca_5(PO_4)_3OH$, $Ca_4O(PO_4)_2$, $CaP_4O_{11}$, $\alpha$-$Ca_2P_2O_7$, $\beta$-$Ca_2P_2O_7$, $\gamma$-$Ca_2P_2O_7$, $Ca(H_2PO_4)_2 \cdot nH_2O$, where n is a real number from 0 to 5, $Ca_8H_2(PO_4)_6 \cdot 5H_2O$, $Ca(SO_4)_2$, $\alpha$-$Ca(SO_4)_2 \cdot 1/2H_2O$, or $\beta$-$Ca(SO_4)_2 \cdot 1/2H_2O$; or any combination thereof; and
    (b) a plurality of fibers that are resorbable homopolymers or copolymers wherein ends of the fibers have shapes of beads, balls, dogbone shapes or dumbbell shapes.

12. The implantable composition of claim 11, further comprising demineralized bone.

13. The implantable composition of claim 11, further comprising a flow additive.

14. The implantable composition of claim 11, further comprising reinforcing fibers.

15. The implantable composition of claim 11, further comprising a radioopaque agent.

16. The implantable composition of claim 11, further comprising one or more of a drug, carrier, bone ingrowth induction catalyst, antiviral, and antibiotic.

17. The implantable composition of claim 11, further comprising one or more of a monofilament, multifilament structure, sheet, coating, membrane, screw augmentation, cranial reconstruction and combinations thereof.

18. A method for forming and implanting an implantable fiber-reinforced composite material, comprising:
    incorporating a sodium hyaluronate flow additive with a calcium salt containing material to form a flowable calcium salt containing composition;
    incorporating a plurality of fibers with the calcium salt containing composition to form a fiber-reinforced calcium salt containing composition;
    positioning continuous reinforcing fibers near, around or within a bone void or a bone defect; and
    introducing the fiber-reinforced calcium salt containing composition into, onto or proximal to a bone void or bone defect in a manner that at least partially coats or fills the bone void or bone defect and continuous reinforcing fibers.

19. The method of claim 18 further comprising incorporating demineralized bone with the fiber-reinforced calcium salt containing composition.

20. An implantable composition comprising:
    (a) a calcium salt-containing component, wherein the calcium salt-containing component is amorphous calcium phosphate, crystalline calcium phosphate, $CaHPO_4$, $CaHPO_4 \cdot H_2O$, $\alpha$-$Ca_3(PO_4)_2$, $\alpha$-bar-$Ca_3(PO_4)_2$, $\beta$-$Ca_3(PO_4)_2$, $\gamma$-$Ca_3(PO_4)_2$, $Ca_5(PO_4)_3OH$, $Ca_4O(PO_4)_2$, $CaP_4O_{11}$, $\alpha$-$Ca_2P_2O_7$, $\beta$-$Ca_2P_2O_7$, $\gamma$-$Ca_2P_2O_7$, $Ca(H_2PO_4)_2 \cdot nH_2O$, where n is a real number from 0 to 5, $Ca_8H_2(PO_4)_6 \cdot 5H_2O$, $Ca(SO_4)_2$, $\alpha$-$Ca(SO_4)_2 \cdot 1/2H_2O$, or $\beta$-$Ca(SO_4)_2 \cdot 1/2H_2O$; or any combination thereof; and (b) from about 1% to about 5% by weight of discrete fibers that are resorbable homopolymers or copolymers, wherein a fiber texture and/or fiber end is modified to increase pullout resistance.

21. The method of claim 18, further comprising grinding the calcium salt containing material.

22. The implantable composition of claim 20, wherein fiber ends have shapes of beads, balls, dogbone shapes or dumbbell shapes.

* * * * *

UNITED STATES PATENT AND TRADEMARK OFFICE
CERTIFICATE OF CORRECTION

PATENT NO. : 7,628,851 B2
APPLICATION NO. : 12/130287
DATED : December 8, 2009
INVENTOR(S) : Bryan M. Armitage et al.

It is certified that error appears in the above-identified patent and that said Letters Patent is hereby corrected as shown below:

In column 2, line 45, delete "$CaHPO_4.H_2O$," and insert -- $CaHPO_4 \cdot H_2O$, --, therefor.

In column 2, line 48, delete "$Ca(H_2PO_4)_2.nH_2O$," and insert -- $Ca(H_2PO_4)_2 \cdot nH_2O$, --, therefor.

In column 2, line 49, delete "$Ca_8H_2(PO_4)_6.5H_2O$" and insert -- $Ca_8H_2(PO_4)_6 \cdot 5H_2O$ --, therefor.

In column 2, lines 50-51, delete "$\alpha$-$Ca(SO_4)_2.1/2H_2O$, $\beta$-$Ca(SO_4)_2 .1/2H_2O$;" and insert -- $\alpha$-$Ca(SO_4)_2 \cdot 1/2H_2O$, $\beta$-$Ca(SO_4)_2 \cdot 1/2H_2O$; --, therefor.

In column 3, line 56, delete "$CaHPO_4.H_2O$," and insert -- $CaHPO_4 \cdot H_2O$, --, therefor.

In column 3, line 59, delete "$Ca(H_2PO_4)_2.nH_2O$," and insert -- $Ca(H_2PO_4)_2 \cdot nH_2O$, --, therefor.

In column 3, line 60, delete "$Ca_8H_2(PO_4)_6.5H_2O$" and insert -- $Ca_8H_2(PO_4)_6 \cdot 5H_2O$ --, therefor.

In column 3, line 62, delete "$\alpha$-$Ca(SO_4)_2 .1/2H_2O$, $\beta$-$Ca(SO_4)_2.1/2H_2O$;" and insert -- $\alpha$-$Ca(SO_4)_2 \cdot 1/2H_2O$, $\beta$-$Ca(SO_4)_2 \cdot 1/2H_2O$; --, therefor.

In column 4, line 12, delete "$CaHPO_4.H_2O$," and insert -- $CaHPO_4 \cdot H_2O$, --, therefor.

In column 4, line 15, delete "$Ca(H_2PO_4)_2.nH_2O$," and insert -- $Ca(H_2PO_4)_2 \cdot nH_2O$, --, therefor.

In column 4, line 16, delete "$Ca_8H_2(PO_4)_6.5H_2O$" and insert -- $Ca_8H_2(PO_4)_6 \cdot 5H_2O$ --, therefor.

In column 4, line 18, delete "$\alpha$-$Ca(SO_4)_2 .1/2H_2O$, $\beta$-$Ca(SO_4)_2.1/2H_2O$;" and insert -- $\alpha$-$Ca(SO_4)_2 \cdot 1/2H_2O$, $\beta$-$Ca(SO_4)_2 \cdot 1/2H_2O$; --, therefor.

In column 4, line 35, delete "$CaHPO_4.H_2O$," and insert -- $CaHPO_4 \cdot H_2O$, --, therefor.

In column 4, line 38, delete "$Ca(H_2PO_4)_2.n H_2O$," and insert -- $Ca(H_2PO_4)_2 \cdot nH_2O$, --, therefor.

Signed and Sealed this

Eighth Day of June, 2010

David J. Kappos
*Director of the United States Patent and Trademark Office*

In column 4, line 39, delete "Ca$_8$H$_2$(PO$_4$)$_6$.5H$_2$O" and insert -- Ca$_8$H$_2$(PO$_4$)$_6$·5H$_2$O --, therefor.

In column 4, line 41, delete "α-Ca(SO$_4$)$_2$.1/2H$_2$O, β-Ca(SO$_4$)$_2$.1/2H$_2$O;" and insert -- α-Ca(SO$_4$)$_2$·1/2H$_2$O, β-Ca(SO$_4$)$_2$·1/2H$_2$O; --, therefor.

In column 7, line 31, delete "CaHPO$_4$.H$_2$O," and insert -- CaHPO$_4$·H$_2$O, --, therefor.

In column 7, lines 33-34, delete "Ca$_8$H$_2$(PO$_4$)$_6$.5H$_2$O, Ca(H$_2$PO$_4$)$_2$.nH$_2$O" and insert -- Ca$_8$H$_2$(PO$_4$)$_6$·5H$_2$O, Ca(H$_2$PO$_4$)$_2$·nH$_2$O --, therefor.

In column 7, line 59, delete "phosphite;" and insert -- phosphate; --, therefor.

In column 7, line 60, delete "α-Ca(SO$_4$)$_2$.1/2H$_2$O or β-Ca(SO$_4$)$_2$.1/2H$_2$O;" and insert -- α-Ca(SO$_4$)$_2$·1/2H$_2$O or β-Ca(SO$_4$)$_2$·1/2H$_2$O; --, therefor.

In column 8, line 28, delete "Ca(H$_2$PO$_4$)$_2$.H$_2$O," and insert -- Ca(H$_2$PO$_4$)$_2$·H$_2$O, --, therefor.

In column 8, line 65, delete "glycolic acid, glycolic acid," and insert -- glycolic acid, --, therefor.

In column 9, line 6, delete "thereof" and insert -- thereof. --, therefor.

In column 9, lines 17-18, delete "arnmonium" and insert -- ammonium --, therefor.

In column 10, line 55, delete "α-propiolactic" and insert -- β-propiolactic --, therefor.

In column 12, line 38, delete "mesh-lactide)" and insert -- meso-lactide) --, therefor.

In column 16, line 55, delete "millijoules" and insert -- milliJoules --, therefor.

In column 23, line 32, delete "thereof;" and insert -- thereof, --, therefor.

In column 23, line 41, delete "thereof;" and insert -- thereof, --, therefor.

In column 23, line 52, delete "thereof;" and insert -- thereof, --, therefor.

In column 24, line 4, delete "thereof;" and insert -- thereof, --, therefor.

In column 24, line 64, delete "sulfite" and insert -- sulfate --, therefor.

In column 25, line 51, delete "Chioroquine," and insert -- Chloroquine, --, therefor.

In column 25, lines 65-66, delete "Chioramphenicol, Florence," and insert -- Chloramphenicol, Florfenicol, --, therefor.

In column 26, line 7, delete "Cefbimizole," and insert -- Cefpimizole, --, therefor.

CERTIFICATE OF CORRECTION (continued)
U.S. Pat. No. 7,628,851 B2

In column 26, line 8, delete "Cefjrozil," and insert -- Cefprozil, --, therefor.

In column 26, line 10, delete "Cefiriaxone," and insert -- Ceftriaxone, --, therefor.

In column 26, line 22, delete "Meziocillin," and insert -- Mezlocillin, --, therefor.

In column 26, line 53, delete "Niftirtoinol," and insert -- Nifurtoinol, --, therefor.

In column 26, line 62, delete "Dichioramine" and insert -- Dichloramine --, therefor.

In column 27, line 5, delete "Sulfamidocbrysoidine," and insert -- Sulfamidochrysoidine, --, therefor.

In column 27, lines 23-24, delete "Butoconazole,Chlordantoin," and insert -- Butoconazole, Chlordantoin, --, therefor.

In column 27, line 42, delete "Chioramphenicol," and insert -- Chloramphenicol, --, therefor.

In column 27, line 51, delete "Chiorhexidine," and insert -- Chlorhexidine, --, therefor.

In column 27, line 64, delete "osteoclasts" and insert -- osteoblasts --, therefor.

In column 28, line 11, delete "TGF-fβ)," and insert -- TGF-β), --, therefor.

In column 28, line 14, delete "(OP-1=BMP -7," and insert -- (OP-1=BMP-7, --, therefor.

In column 38, line 28, delete "Na2HPO4" and insert -- $Na_2HPO_4$ --, therefor.

In columns 37-38, line 5, in "Table 5", delete "Na2HPO4" and insert -- $Na_2HPO_4$ --, therefor.

In column 40, line 61, delete "Na2HPO4" and insert -- $Na_2HPO_4$ --, therefor.

In column 42, line 20, delete "25°," and insert -- 25° C., --, therefor.

In column 42, line 64, delete "$Na_2HPO_4.7H_2O$" and insert -- $Na_2HPO_4 \cdot 7H_2O$ --, therefor.

In column 42, line 65, delete "$NaH_2PO_4.H_2O$" and insert -- $NaH_2PO_4 \cdot H_2O$ --, therefor.

In column 43, line 29, in Claim 1, delete "$CaHPO_4.H_2O$," and insert -- $CaHPO_4 \cdot H_2O$, --, therefor.

In column 43, line 32, in Claim 1, delete "$Ca(H_2PO_4)_2.nH_2O$," and insert -- $Ca(H_2PO_4)_2 \cdot nH_2O$, --, therefor.

In column 43, line 33, in Claim 1, delete "$Ca_8H_2(PO_4)_6.5H_2O$," and insert -- $Ca_8H_2(PO_4)_6 \cdot 5H_2O$, --, therefor.

CERTIFICATE OF CORRECTION (continued)
U.S. Pat. No. 7,628,851 B2

In column 43, lines 34-35, in Claim 1, delete "α-Ca(SO$_4$)$_2$.1/2H$_2$O, or β-Ca(SO$_4$)$_2$.1/2H$_2$O;" and insert -- α-Ca(SO$_4$)$_2$·1/2H$_2$O, or β-Ca(SO$_4$)$_2$·1/2H$_2$O; --, therefor.

In column 43, line 59, in Claim 7, delete "CaHPO$_4$.H$_2$O," and insert -- CaHPO$_4$·H$_2$O, --, therefor.

In column 43, line 62, in Claim 7, delete "Ca(H$_2$PO$_4$)$_2$.nH$_2$O," and insert -- Ca(H$_2$PO$_4$)$_2$·nH$_2$O, --, therefor.

In column 43, line 63, in Claim 7, delete "Ca$_8$H$_2$(PO$_4$)$_6$.5H$_2$O," and insert -- Ca$_8$H$_2$(PO$_4$)$_6$·5H$_2$O, --, therefor.

In column 43, line 64, in Claim 7, delete "α-Ca(SO$_4$)$_2$.1/2H$_2$O, or β-Ca(SO$_4$)$_2$.1/2H$_2$O;" and insert -- α-Ca(SO$_4$)$_2$·1/2H$_2$O, or β-Ca(SO$_4$)$_2$·1/2H$_2$O; --, therefor.

In column 44, line 17, in Claim 11, delete "CaHPO$_4$.H$_2$O," and insert -- CaHPO$_4$·H$_2$O, --, therefor.

In column 44, line 20, in Claim 11, delete "Ca(H$_2$PO$_4$)$_2$.nH$_2$O," and insert -- Ca(H$_2$PO$_4$)$_2$·nH$_2$O, --, therefor.

In column 44, line 21, in Claim 11, delete "Ca$_8$H$_2$(PO$_4$)$_6$.5H$_2$O," and insert -- Ca$_8$H$_2$(PO$_4$)$_6$·5H$_2$O, --, therefor.

In column 44, line 22, in Claim 11, delete "α-Ca(SO$_4$)$_2$.1/2H$_2$O, or β-Ca(SO$_4$)$_2$.1/2H$_2$O;" and insert -- α-Ca(SO$_4$)$_2$·1/2H$_2$O, or β-Ca(SO$_4$)$_2$·1/2H$_2$O; --, therefor.

In column 44, line 34, in Claim 15, delete "radioopaque" and insert -- radiopaque --, therefor.

In column 44, line 64, in Claim 20, delete "CaHPO$_4$.H$_2$O," and insert -- CaHPO$_4$·H$_2$O, --, therefor.

In column 44, line 67, in Claim 20, delete "Ca(H$_2$PO$_4$)$_2$.nH$_2$O," and insert -- Ca(H$_2$PO$_4$)$_2$·nH$_2$O, --, therefor.

In column 45, line 1, in Claim 20, delete "Ca$_8$H$_2$(PO$_4$)$_6$.5H$_2$O," and insert -- Ca$_8$H$_2$(PO$_4$)$_6$·5H$_2$O, --, therefor.

In column 45, lines 1-2, in Claim 20, delete "α-Ca(SO$_4$)$_2$.1/2H$_2$O, or β-Ca(SO$_4$)$_2$.1/2H$_2$O;" and insert -- α-Ca(SO$_4$)$_2$·1/2H$_2$O, or β-Ca(SO$_4$)$_2$·1/2H$_2$O; --, therefor.